(12) United States Patent
Hong et al.

(10) Patent No.: US 6,787,551 B2
(45) Date of Patent: Sep. 7, 2004

(54) THIAZOLIDINEDIONE DERIVATIVES AND PHARMACEUTICAL COMPOSITION COMPRISING THE SAME

(75) Inventors: Chung-Il Hong, Chicago, IL (US);
Soon-Kil Ahn, Kangnam-gu (KR);
Bok-Young Kim, Suwon-si (KR);
Joong-Bok Ahn, Asan-si (KR);
Do-Young Lee, Nam-gu (KR);
Hong-Woo Lee, Ansan-si (KR);
Jae-Soo Shin, Seocho-gu (KR)

(73) Assignee: Chong Kun Dang Pharmaceutical Corporation, Seoul (KR)

( * ) Notice: Subject to any disclaimer, the term of this patent is extended or adjusted under 35 U.S.C. 154(b) by 0 days.

(21) Appl. No.: 10/250,502

(22) PCT Filed: Mar. 28, 2002

(86) PCT No.: PCT/KR02/00542
§ 371 (c)(1),
(2), (4) Date: Jul. 3, 2003

(87) PCT Pub. No.: WO03/080605
PCT Pub. Date: Oct. 2, 2003

(65) Prior Publication Data
US 2004/0122031 A1 Jun. 24, 2004

(30) Foreign Application Priority Data
Mar. 22, 2002 (KR) .......................... 2002-15755

(51) Int. Cl.[7] .................... C07D 401/12; C07D 417/12; A61K 31/427
(52) U.S. Cl. ...................... 514/256; 514/269; 514/342; 544/326; 544/327; 546/269.7
(58) Field of Search ............................... 544/326, 327; 546/269.7; 514/256, 269, 342

(56) References Cited

U.S. PATENT DOCUMENTS

| | | | |
|---|---|---|---|
| 5,441,971 A | 8/1995 | Sohda et al. | 514/342 |
| 5,708,012 A | 1/1998 | Olefsky | 514/337 |

FOREIGN PATENT DOCUMENTS

| | | |
|---|---|---|
| EP | 0842925 | 5/1998 |
| WO | 98-55121 | 12/1998 |

OTHER PUBLICATIONS

Gurram R. Madhavan, et al., "Novel phthalazinone and benzoxazinone containing thiazolidinediones as antidiabetic and hypolipidemic agents" In European Journal of Medicinal Chemistry, vol. 36, 2001, p. 627–37.

Miuoru Oguchi, et al., *J. Med. Chem.*, 2000, 43, 3052–3066.

B.B. Lohray, et al., *J. Med. Chem.*, 1999, 42, 2569–2581.

Braj. B. Lohray, V. Bhushan, et al., *Bioorg. Med. Chem. Lett.*, 1997, 7(7), 785–788.

Kelving. Liu, et al., *Bioorg. Med. Chem. Lett.*, 2001, 11, 2385–2388.

T. M. Willson et al., *J. Med. Chem.*, 2000, 43(4), 527–550.

Jeffrey. E. Cobb, et al., *J. Med. Chem.*, 1996, 39, 665–668.

*J. Med. Chem.*, 1998, 41, 5055–5069.

John L. Collins, et al., *J. Med. Chem.*, 1998, 41, 5037–5054.

Hisashi Shinkai et al., *J. Med. Chem.*, 1998, 41, 1927–1933.

*Primary Examiner*—Deepak Rao
(74) *Attorney, Agent, or Firm*—Venable LLP; Richard D. Schmidt

(57) ABSTRACT

The present invention relates to a thiazolidinedione derivative, represented in formula (1) below, pharmaceutically acceptable salts thereof, and/or pharmaceutically acceptable solvates thereof. Further, the present invention provides a pharmaceutical composition comprising the compound represented in formula (1) below, Formula (1)

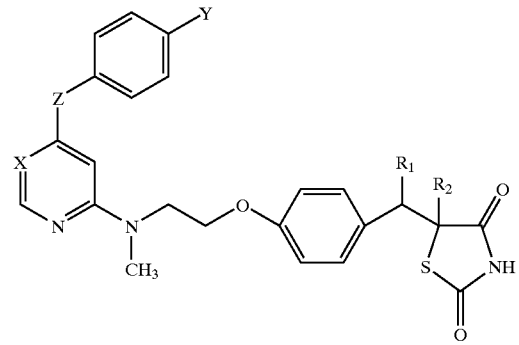

wherein:

X represents a carbon or nitrogen atom, Y represents a hydrogen atom, an alkyl group, an alkoxy group, a halogen, or an aryl group, Z represents an oxygen, nitrogen, or sulfur atom, and $R_1$ and $R_2$ each represent a hydrogen atom; or $R_1$ and $R_2$ together form a bond.

10 Claims, No Drawings

THIAZOLIDINEDIONE DERIVATIVES AND PHARMACEUTICAL COMPOSITION COMPRISING THE SAME

TECHNICAL FIELD

The present invention relates to a thiazolidinedione derivative, represented in formula (1) below, a pharmaceutically acceptable salt thereof, or a pharmaceutically acceptable solvate thereof. Further, the present invention provides a pharmaceutical composition comprising the compound represented in formula (1) below.

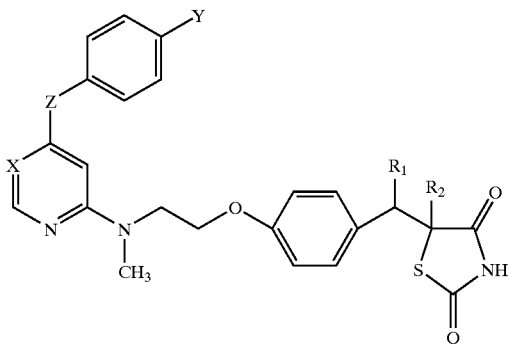

Formula (1)

wherein:

X represents a carbon or nitrogen atom; Y represents a hydrogen atom, an alkyl group, an alkoxy group, a halogen, or an aryl group; Z represents an oxygen, nitrogen, or sulfur atom; and $R_1$ and $R_2$ each represent a hydrogen atom, or $R_1$ and $R_2$ together form a bond.

BACKGROUND ART

Thiazolidinedione based compounds are oral diabetes therapeutic agents for treating insulin resistance, using a new mechanism different from that of conventional diabetes therapeutic agents. They lower blood sugar level by increasing physiological effects of insulin on target cells (muscle, adipocytes, liver, etc.). Now, the thiazolidinedione based compounds are highlighted as new diabetes therapeutic agents. Further, it has been reported in several documents that as insulin, free fatty acid, and triglyceride, etc. accumulate to high levels in the body, the thiazolidinedione based compounds strongly suppress further synthesis (Miuoru Oguchi, et al., *J.Med. Chem.*, 2000, 43, 3052–3066; B. B. Lohray, et al., *J. Med. Chem.*, 1999, 42, 2569–2581; Braj. B. Lohray, V. Bhushan, et al., *Bioorg. Med. Chem. Lett.*, 1997, 7(7), 785–788; Kelving. Liu, et al., *Bioorg. Med. Chem. Lett.*, 2001, 11, 2385–2388; T. M. Willson et al., *J. Med. Chem.*, 2000, 43(4), 527–550; Jeffery, E. Cobb, et al., *J. Med. Chem.*, 1996, 39, 665–668; *J. Med. Chem.*, 1998, 41, 5055–5069; John L. Collins, et al., *J. Med. Chem.*, 1998, 41, 5037–5054; Hisashi Shinkai et al., *J. Med. Chem.*, 1998, 41, 1927–1933).

Rosiglitazone is commercially available. It is the strongest thiazolidinedione based compound discovered until now. It has been disclosed in European Patent Laid-Open Publication No. 0,842,925 and a journal (J. Med. Chem., 1994, 37, 3977–3985), which are incorporated herein by reference.

Rosiglitazone, having a structure similar to that of the present invention, is represented in formula (2) below.

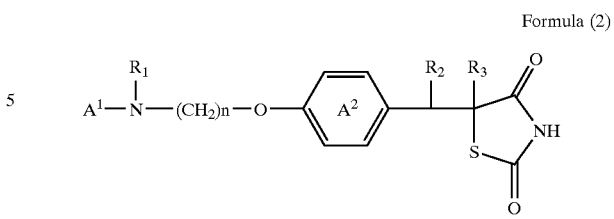

Formula (2)

wherein, $A^1$ is formula (a) or (b) below:

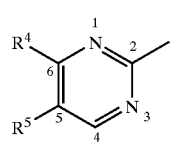

(a)

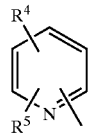

(b)

wherein, $R^4$ and $R^5$ each independently represent a hydrogen atom, an alkyl group or a substituted or unsubstituted aryl group, or when $R^4$ and $R^5$ are each attached to adjacent carbons, $R^4$ and $R^5$ together with the carbon atoms to which they are attached form a benzene ring, in which each carbon atom represented by $R^4$ and $R^5$ together may be substituted or unsubstituted.

Rosiglitazone exhibits a moderate blood sugar-lowering effect, but has little activity versus hyperlipidemia, which is common in patients with diabetes. Furthermore, because its half life is short in terms of pharmacodynamics, it must be inconveniently administered twice a day. In rare cases, it has been clinically reported that liver toxicity involved in use of rosiglitazone drugs causes death. Therefore, there is a disadvantage in that the patients with diabetes must have their liver function tested periodically.

DISCLOSURE OF THE INVENTION

Therefore, the present invention has been made in view of the above problems, and it is an object of the present invention to provide a new thiazolidinedione based compound having activities such as strong blood sugar lowering action and strong blood lipid lowering action, compared with rosiglitazone, and a pharmaceutical composition containing the thiazolidinedione based compound.

It is another object of the present invention to provide a new thiazolidinedione based compound, in which its half-life is remarkably prolonged, and a pharmaceutical composition containing the thiazolidinedione based compound.

It is yet another object of the present invention to provide a new thiazolidinedione based compound, in which liver toxicity, a common side effect encountered with this type of compound drug, is not found, and a pharmaceutical composition containing the thiazolidinedione based compound.

BEST MODE FOR CARRYING OUT THE INVENTION

To overcome disadvantages of rosiglitazone described above, the inventors have researched documents concerning thiazolidinedione based compounds for several years. At the same time, they have studied the relationship of the thiazolidinedione based drug and its receptor using computer-aided molecular design.

According to the X-ray crystal structure of a PPARγ (peroxisome proliferator activated receptor), a molecule that influences insulin resistance, it has been found that part of the lipophilic tail thereof consists of hydrophobic residues such as isoleucine, valine, leucine, etc. Also, the size of active site thereof is very large, and the length and volume of the site are sufficient for about two hexagonal aromatic rings to be introduced into the site. Based on these facts, the inventors made an every efforts to develop new drugs with excellent functional groups, binding strongly with the PPARγ, a molecule that influences insulin resistance. As a result, they induced a substituted or unsubstituted aryl structure, i.e. a substituted or unsubstituted pyridine or pyrimidine, in which a nitrogen, an oxygen or a sulfur atom is incorporated at the para position of the first nitrogen of the pyridine or pyrimidine, i.e., at the 4 position. By preparing a thiazolidinedione based compound containing the aryl structure in the laboratory and then assaying its pharmacological toxicity, the present inventors have found it to be a new and excellent thiazolidinedione derivative for treatment of diabetes.

In terms of the structure of rosiglitazone of formula (2) above compared with the present invention of the formula (1), $A^1$ in the formula (2) is pyrimidine or pyridine, which corresponds to the pyrimidine (X=N) or pyridine (X=C) of the formula (1). As for the pyrimidine, an amine is bound at C-2 position in rosiglitazone, while an amine is bound at C-6 position in the present invention. Furthermore, the present invention has a substituted or unsubstituted aryl (phenyl) group, in which an oxygen, a nitrogen or a sulfur atom may exist at C-4 position of the pyrimidine or pyridine. Specifically, the substituent is incorporated at the para position of the pyrimidine or pyridine, which is the most stable position in terms of chemical structure, thereby a stable molecular structure being obtained. In addition to the above, according to the computer-aided molecular design (SAR), the active site of the PPARγ which is a molecule that influences insulin resistance, is three-dimensionally suitable for accepting the structure of the present invention compound, thereby the high pharmaceutical effect of the present invention compound being obtained. Accordingly, the present invention has a three dimensional structure distinguishable from a conventional rosiglitazone.

The present invention exhibits a strong blood sugar lowering activity and a strong blood lipid lowering activity, thereby capable of being used in the treatment or prevention of hyperglycemia. In particular, it has been found that the present invention is useful for the treatment of type II diabetes.

Further, it has been found that the present invention can be used in the treatment and/or prevention of other diseases such as hyperlipidemia, hypertension, cardiovascular disease and bulimia.

Accordingly, the present invention provides a thiazolidinedione derivative, represented in formula (1) below, a pharmaceutically acceptable salt thereof, and/or a pharmaceutically acceptable solvate thereof.

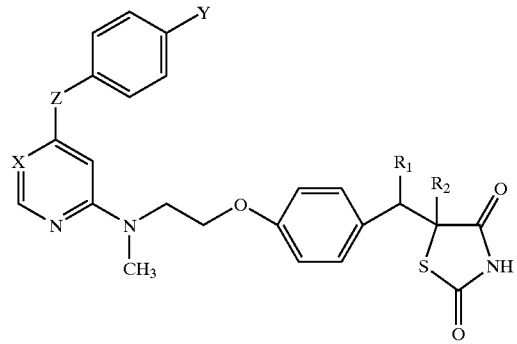

Formula (1)

wherein:
X represents a carbon or nitrogen atom; Y represents a hydrogen atom, an alkyl group, an alkoxy group, a halogen, or an aryl group; Z represents an oxygen, nitrogen, or sulfur atom; and $R_1$ and $R_2$ each represent a hydrogen atom, or $R_1$ and $R_2$ together form a bond.

When X is a carbon atom, Y represents a hydrogen atom, an alkyl group, an alkoxy group, a halogen, or an aryl group. Preferably, the alkyl group is a $C_1$–$C_4$ lower alkyl group such as methyl, ethyl, n-propyl or isopropyl, n-butyl, isobutyl or tert-butyl, with the ethyl and isopropyl being more preferable.

The alkoxy group is preferably a $C_1$–$C_3$ lower alkoxy group such as methoxy, ethoxy, propoxy, or isopropoxy, with the methoxy being more preferable.

The halogen is fluorine, chlorine, bromine or iodine, with the chlorine or fluorine being preferred.

The aryl group is a phenyl group or a substituted phenyl group, with the phenyl group being preferred.

When X is a nitrogen atom, Y represents a hydrogen atom, an alkyl group, an alkoxy group, a halogen or an aryl group. Preferably, the alkyl group is a $C_1$–$C_4$ lower alkyl group such as methyl, ethyl, n-propyl or isopropyl, n-butyl, isobutyl or tert-butyl, with the ethyl and isopropyl being more preferable.

The alkoxy group is preferably a $C_1$–$C_3$ lower alkoxy group such as methoxy, ethoxy, propoxy or isopropoxy, with the methoxy being more preferable.

The halogen is fluorine, chlorine, bromine or iodine, with the chlorine and fluorine being preferred.

The aryl group is a phenyl group or a substituted phenyl group, with the phenyl group being preferred.

Certain of the compounds represented by the formula (1) can be present in the form of tautomeric isomers, all of which are encompassed by the present invention. Certain of the compounds of the present invention also possess one or more chiral centers. The compounds can, therefore, form stereoisomers. The present invention includes the use of both the individual, isolated isomers and mixtures thereof. Pharmaceutically acceptable salts thereof and pharmaceutically acceptable solvates thereof also are all embraced by the present invention.

The pharmaceutically acceptable base addition salts of the compounds of the present invention include, for example, salts with metal such as aluminium, alkali metals such as lithium, sodium and potassium, and alkaline earth metals such as calcium and magnesium, and ammonium salts or substituted ammonium salts. The substituted ammonium salts include, for example, salts with lower alkylamine such as triethylamine, hydroxyalkylamine such as 2-hydroxyethylamine, bis-(2-hydroxyethyl)amine or tri-2- hydroxyethyl)amine, cycloalkylamine such as bicyclohexylamine, or salts with procaine, dibenzylpiperazine, N-benzyl-β-penethylamine, dehydroabiethylamine, N,N'-bisdehydroabiethylamine, glucamine, N-methylglucamine, or pyridine bases such as pyridine, collidine or quinoline.

The pharmaceutically acceptable acid addition salts of the compounds of the present invention include, for example, salts derived from inorganic acids (hydrochloride, sulfate, phosphate, hydrobromide), as well as salts derived from organic acids (malate, succinate, fumarate, maleate, tartrate, and sulfonate (methanesulfonate, benzenesulfonate, toluenesulfonate, etc.)).

The compound of the present invention may exist in the form of a hydrate.

In accordance with another embodiment, the present invention provides a method for manufacturing the compound represented by the formula (1), comprising reaction of the compound of formula (3) with the compound of formula (4).

Formula (3)

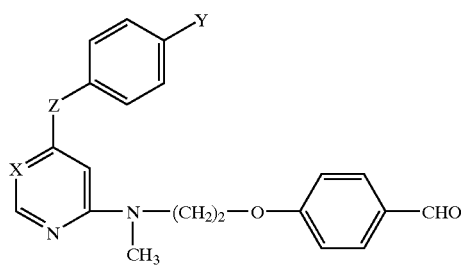

wherein, X, Y and Z are as defined in the formula (1).

Formula (4)

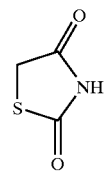

The reaction is carried out at a temperature of 30 to 120° C. in an organic solvent such as toluene, benzene or ethanol. Preferably, the reaction may be carried out in the present of a suitable catalyst such as pyperidine, pyperidinium acetate or benzoate.

If desired, after the above reaction, any suitable conversions may be accomplished as follows:
  (i) where $R_1$ and $R_2$ of the above reaction product together form a bond, reduction of the reaction product to the compound of the formula (1), in which $R_1$ and $R_2$ each represent a hydrogen atom.
  (ii) conversion of above reaction product into a pharmaceutically acceptable salt thereof or a pharmaceutically acceptable solvate thereof The conversions can be carried out using suitable conventional conversion processes. A suitable reduction method is a reduction method using a catalyst or a metal/solvent reduction system. In the catalytic reduction, a catalyst suitable for use is palladium on carbon, i.e., 10% palladium on charcoal or 20% palladium hydroxide on charcoal. The catalytic reduction can be carried out in a solvent such as dimethylformamide, methanol, dioxane, and ethylacetate with the methanol being preferred. The suitable metal/solvent reduction system includes magnesium in methanol.

The compound represented by the formula (3) can be readily prepared by reacting the compound of formula (5) and the compound of formula (6), below.

Formula (5)

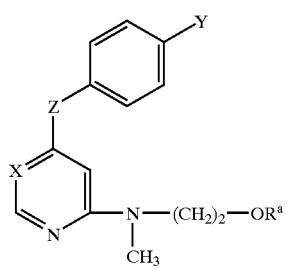

wherein, X, Y and Z are as defined in the formula (1), $R^a$ represents a hydrogen, a tosylate or a mesylate group.

Formula (6)

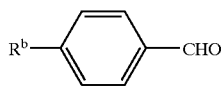

wherein, $R^b$ represents a hydroxyl group or a halogen atom.

Where $R^a$ is a hydrogen, and $R^b$ is a halogen atom, in particular, a fluorine atom, the reaction of (5) with (6) can be carried out at a temperature of 25 to 150° C., in a solvent such as dimethylformamide or dimethylsulfoxide, preferably in the presence of a base such as sodium hydroxide or potassium carbonate.

Where $R^a$ is a hydrogen, and $R^b$ is a hydroxyl group, the reaction can be appropriately carried out at room temperature in an aprotic solvent such as tetrahydrofuran in the presence of a coupling agent such as triphenylphosphine and diethylazodicarboxylate.

Where $R^a$ is a tosylate or mesylate, and $R^b$ is a hydroxyl group, the reaction can be carried out at a temperature of 0 to 120° C., in an aprotic solvent such as dimethylformamide in the presence of a base such as sodium hydroxide.

The compound of the formula (5), in which $R^a$ is a tosylate or a mesylate, can be prepared by reacting the compound (5), $R^a$ being a hydrogen, with a tosyl halide or a mesyl halide.

The compound of the formula (6) is a known compound, or can be prepared using a method similar to that used to prepare the known compound. For example, 4-fluorobenzaldehyde and 4-hydroxybenzaldehyde are compounds commercially available.

The compound of the formula (5) can be prepared by reacting the compound of formula (7) and the compound of formula (8), below.

Formula (7)

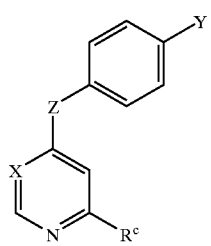

wherein, $R^c$ is a leaving group. The suitable leaving group includes a halogen atom, preferably a chlorine or a fluorine atom, or a thioalkyl group (for example, a thiomethyl group).

 Formula (8)

The reaction of (7) with (8) is carried out at a temperature of 0 to 120° C., in a solvent such as dichloromethane, ethanol or toluene, preferably ethanol. Per 1 equivalent of the compound (7), 1 to 10 equivalents of the compound (8), preferably 2 to 4 equivalents can be used.

The compound (7) can be obtained by using the compound (9) or the compound (10) below as a starting material and reacting reactants under suitable reaction conditions.

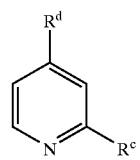 Formula (9)

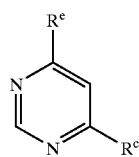 Formula (10)

wherein, $R^d$ and $R^e$ are leaving groups. $R^d$ is a halogen atom, such as fluorine, chlorine, bromine and iodine, or a nitrogroup, with the nitrogroup being preferred.

$R^e$ is a halogen atom such as fluorine, chlorine, bromine and iodine, with the fluorine and the chlorine being preferred.

The compound (7), in which Z is an oxygen or a sulfur atom, is prepared by reacting the compound (9) or (10) with a substituted or unsubstituted sodium phenoxide or sodium thiophenoxide. In this case, the reaction solvent to be used is tetrahydrofuran, N,N-dimethylformamide, N,N,-dimethylacetamide, 1,4-dioxane, or diethylether. More preferably, the N,N-dimethylformamide or the N,N-dimethylacetamide can be used. The reaction temperature is in the range of 0 to 120° C., preferably 0 to 50° C., and more preferably 0 to 25° C.

The compound (7), in which Z is a nitrogen atom; is prepared by reacting the compound (9) or (10) and a substituted or unsubstituted aniline. The suitable reaction solvent is N-butylamine or N-methylpyrolidin-2-one. The N-methylpyrolidin-2-one is preferred. The reaction temperature is in the range of 0 to 200° C., and preferably 50 to 120° C.

As can be seen from the foregoing, the present invention provides the compound of the formula (1) and/or a pharmaceutically acceptable salt thereof and/or a pharmaceutically acceptable solvate thereof.

Further, the present invention provides the compound of the formula (1) and/or a pharmaceutically acceptable salt thereof and/or a pharmaceutically acceptable solvate thereof, useful for the treatment and prevention of hyperglycemia and hyperlipidemia.

Still further, the present invention provides the compound of the formula (1), and/or a pharmaceutically acceptable salt thereof and/or a pharmaceutically acceptable solvate thereof, useful for the treatment of hypertension, cardiovascular disease and bulimia.

The compound of the formula (1) and/or a pharmaceutically acceptable salt thereof and/or a pharmaceutically acceptable solvate thereof can be administered alone or in combination with a pharmaceutically acceptable carrier.

Accordingly, the present invention also provides a pharmaceutical composition which comprises the compound of the formula (1) and/or a pharmaceutically acceptable salt thereof and/or a pharmaceutically acceptable solvate thereof in combination with a pharmaceutically acceptable carrier.

In general, the composition of the present invention may be formulated for administration by any convenient route, e.g. by injection or by epidermal absorption. Oral administration can also be used. In particular, orally administrable compositions may take any convenient form, i.e. unit dosage form including, for example, tablets, capsules or powders in vials or ampules.

Carriers that are widely employed in ordinary pharmaceuticals include, for example, diluents, fillers, disintegrators, wetting agents, lubricants, coloring agents, flavoring agents or other adjuvants.

Suitable carriers are, for example, crystalline cellulose, starch, sodium starch glycolate, polyvinylpyrolidone, polyvinylpolypyrolidone, magnesium stearate, sodium laurylsulfate or sucrose.

Above compositions are suitably formulated in unit dosage form. The unit dosage form may generally include a dose of 0.1–1,000 mg of the active ingredient in the composition of the present invention, preferably 0.1–500 mg, and most preferably 0.1–250 mg.

For the treatment and prevention of hyperglycemia and hyperlipidemia, in an average 70 kg adult, the active ingredient can be administered at a dose of 0.1–6,000 mg/day. The composition containing the active ingredient can be administered in about 1 to 6 portions in a day. In this case, a dose of the active ingredient in a portion may be generally chosen within the range of about 1 to 1,500 mg.

The dose for the treatment of hypertension, cardiovascular disease or bulimia also is as mentioned above.

For the treatment and prevention of hyperglycemia in mammals except for humans, in particular canines, the active ingredient can be orally administered in the form of a dose of 0.025 mg/kg–25 mg/kg once or twice a day. The above dose also can be applied for the treatment and prevention of hyperlipidemia in mammals except for humans.

EXAMPLES

The present invention will hereinafter be described more specifically by preparations and examples. It is, however, to be borne in mind that the present invention is by no means limited to or by them.

Preparation 1
4-Phenoxy-6-chloropyrimidine

To a solution of phenol (1.1 g) in dimethylformamide (20 mL) was slowly added sodium hydride (60%, 805 mg) at 0° C. After the resultant mixture was stirred at 0° C. for 30 minutes, 4,6-dichloropyrimidine (1.5 g) was added, followed by stirring at 25° C. for 1 hour and then addition of saturated aqueous ammonium chloride solution (20 mL). Then, the obtained mixture was diluted with ethyl acetate (50 mL) and washed three times with brine (30 mL each time). An organic layer was separated, dried ($MgSO_4$) and filtered. The filtrate was concentrated under reduced pressure. The title compound (1.2 g) was obtained by silica gel column chromatography (ethyl acetate/n-hexane=1/10).

$^1$H NMR $\delta$($CDCl_3$): 6.9(1H, s), 7.15(2H, m), 7.35(1H, m), 7.6(2H, m), 8.6(1H, s).

Preparation 2
2-[N-methyl-N-(6-(4-phenoxy)-pyrimidinyl)amino]ethanol

To a solution of 4-phenoxy-6-chloro-pyrimidine (1.8 g) in ethanol (30 mL) was added 2-methylaminoethanol (1 g), followed by stirring under reflux for 24 hours. The resultant mixture was cooled to room temperature, diluted with ethyl acetate (50 mL), washed three times with brine (30 mL each time) and an organic layer was separated. The organic layer so separated was dried ($MgSO_4$) and filtered. The filtrate was concentrated under reduced pressure. The title compound (1.5 g) was obtained by silica gel column chromatography (ethyl acetate/n-hexane=1/1).

$^1$H NMR δ($CDCl_3$): 3.05(3H, s), 3.7(2H, m), 3.85(2H, m), 5.85(1H, s), 7.15(2H, m), 7.25(1H, m), 7.45(2H, m), 8.20(1H, s).

Preparation 3
4-[2-(N-methyl-N-(6-(4-phenoxy)-pyrimidinyl)amino)ethoxy]benzaldehyde To a solution of 2-[N-methyl-(6-(4-phenoxy)pyrimidinyl)amino]ethanol (1.02 g) in dimethylformamide (40 mL) was slowly added sodium hydride (60%, 333 mg) at 0° C. After the resultant mixture was stirred at 0° C. for 30 minutes, 4-fluorobenzaldehyde (770 mg) was slowly dropwise added thereto, followed by stirring at 25° C. for 5 hours, and then addition of saturated aqueous ammonium chloride solution (20 mL). Then, the obtained mixture was twice extracted with ethyl acetate (50 mL each time) to separate an organic layer. The organic layer so separated was dried ($MgSO_4$) and filtered. The filtrate was concentrated under reduced pressure. The title compound (1 g) was obtained by silica gel column chromatography (ethyl acetate/n-hexane=1/3).

$^1$H NMR δ($CDCl_3$): 3.15(3H, s), 4.06(2H, m), 4.29(2H, m), 5.9(1H, s), 7.01(2H, m), 7.13(2H, m), 7.28(2H, m), 7.42(2H, m), 7.85(2H, m), 8.33(1H, s), 9.91(1H, s).

Preparation 4
4-Anilinyl-6-chloropyrimidine 4,6-Dichloropyrimidine (1 g) and aniline (746 mg) were added to N-methylpyrolidin-2-one (20 mL) and stirred at 120° C. for 24 hours. The resultant mixture was cooled to room temperature, to which ethyl acetate (30 mL) and brine (30 mL) were added, and stirred for 30 minutes. An organic layer was separated, dried ($MgSO_4$), filtered and then concentrated under reduced pressure. The title compound (950 mg) was obtained by silica gel column chromatography (ethyl acetate/n-hexane=1/5).

$^1$H NMR δ($CDCl_3$): 6.72(1H, s), 7.28(1H, m), 7.33(2H, m), 7.45(2H, m), 7.65(1H, s), 8.46(1H, s).

Preparation 5
4-Phenoxy-2-chloropyridine

The title compound (1.2 g) was prepared by the same procedure as the preparation 1 except for using 2-chloro-4-nitropyridine (2.5 g) and phenol (1.3 g).

$^1$H NMR δ($CDCl_3$): 6.81(1H, m), 6.83(1H, s), 7.12(2H, m), 7.29(1H, m), 7.45(2H, m), 8.24(1H, d).

Preparation 6
4-(4-Fluoro)phenoxy-6-chloropyrimidine

The title compound (2.0 g) was prepared by the same procedure as the preparation 1 except for using 4,6-dichloropyrimidine (2.5 g) and 4-fluorophenol (2.3 g).

$^1$H NMR δ($CDCl_3$): 6.93(1H, s), 7.11(4H, m), 8.58(1H, s), 7.29(1H, m), 7.45(2H, m), 8.24(1H, d).

Preparation 7
4-(4-Chloro)phenoxy-6-chloropyrimidine

The title compound (2.1 g) was prepared by the same procedure as the preparation 1 except for using 4,6-dichloropyrimidine (2.5 g) and 4-chlorophenol (2.2 g).

$^1$H NMR δ($CDCl_3$): 6.95(1H, s), 7.09(2H, m), 7.41(2H, m), 8.58(1H, s).

Preparation 8
4-(4-Methoxy)phenoxy-6-chloropyrimidine

The title compound (2.1 g) was prepared by the same procedure as the preparation 1 except for using 4,6-dichloropyrimidine (2.5 g) and 4-methoxyphenol (2.3 g).

$^1$H NMR δ($CDCl_3$): 3.85(3H, s), 6.90(1H, m), 6.98(2H, m), 7.07(2H, m), 8.60(1H, s).

Preparation 9
4-(4-Ethoxy)phenoxy-6-chloropyrimidine

The title compound (1.8 g) was prepared by the same procedure as the preparation 1 except for using 4,6-dichloropyrimidine (2.5 g) and 4-ethoxyphenol (2.3 g).

$^1$H NMR δ($CDCl_3$): 1.33(3H, m), 3.98(2H, m), 4.25(2H, m), 6.91(1H, m), 6.98(2H, m), 7.13(21H, m), 8.56(1H, s).

Preparation 10
4-(4-Isopropoxy)phenoxy-6-chloropyrimidine

The title compound (1.9 g) was prepared by the same procedure as the preparation 1 except for using 4,6-dichloropyrimidine (2.5 g) and 4-isopropoxy phenol (2.3 g).

$^1$H NMR δ($CDCl_3$): 1.38(6H, s), 4.05(1H, m), 6.94(1H, s), 6.94(2H, m), 7.11(2H, m), 8.63(1H, s).

Preparation 11
4-(4-Methyl)phenoxy-6-chloropyrimidine

The title compound (3.5 g) was prepared by the same procedure as the preparation 1 except for using p-cresol (5.2 g).

$^1$H NMR δ($CDCl_3$): 2.35(3H, s), 6.94(1H, s), 6.97(2H, m), 7.08(2H, m), 8.64(1H, s).

Preparation 12
4-4-Ethyl)phenoxy-6-chloropyrimidine

The title compound (2.8 g) was prepared by the same procedure as the preparation 1 except for using 4-ethylphenol (3.5 g).

$^1$H NMR δ($CDCl_3$): 1.24(3H, m), 4.25(2H, m), 6.96(1H, s), 7.45(3H, m), 7.68(2H, m), 8.71(1H, s).

Preparation 13
4-(4-Isopropyl)phenoxy-6-chloropyrimidine

The title compound (2.5 g) was prepared by the same procedure as the preparation 1 except for using 4isopropylphenol (3.0 g).

$^1$H NMR δ($CDCl_3$): 1.33(6H, s), 3.12(1H, m), 6.92(1H, s), 6.99(2H, m), 7.04(2H, m), 8.65(1H, s).

Preparation 14
4-(4-Phenyl)phenoxy-6-chloropyrimidine

The title compound (2.1 g) was prepared by the same procedure as the preparation 1 except for using 4-phenylphenol (2.7 g).

$^1$H NMR δ($CDCl_3$): 6.99(1H, s), 7.25(2H, m), 7.41(1H, m), 7.48(2H, m), 7.61(2H, m), 7.68(2H, m), 8.64(1H, s).

Preparation 15
4-Thiophenoxy-6-chloropyrimidine

The title compound (2.1 g) was prepared by the same procedure as the preparation 1 except for using thiophenol (2.9 g).

¹H NMR δ(CDCl₃): 6.83(1H, s), 7.42(3H, m), 7.63(2H, s), 8.35(1H, s).

Preparation 16
4-(4-Fluoro)phenoxy-2-chloropyridine

The title compound (2.9 g) was prepared by the same procedure as the preparation 1 except for using 4-fluorophenol (5.2 g).

¹H NMR δ(CDCl₃): 6.79(2H, m), 7.08(2H, m), 7.15(2H, m), 8.26(1H, m).

Preparation 17
4-(4-Chloro)phenoxy-2-chloropyridine

The title compound (3.2 g) was prepared by the same procedure as the preparation 1 except for using 4-chlorophenol (3.9 g).

¹H NMR δ(CDCl₃): 6.79(2H, m), 7.05(2H, m), 7.42(2H, m), 8.25(1H, m).

Preparation 18
4-(4-Methoxy)phenoxy-6-chloropyridine

The title compound (3.8 g) was prepared by the same procedure as the preparation 1 except for using 4-methoxyphenol (4.6 g).

¹H NMR δ(CDCl₃): 3.75(3H, s), 6.77(2H, m), 7.09(2H, m), 7.45(2H, m), 8.29(1H, m).

Preparation 19
4-(4-Isopropyl)phenoxy-2-chloropyridine

The title compound (3.0 g) was prepared by the same procedure as the preparation 1 except for using 4-isopropylphenol (3.8 g).

¹H NMR δ(CDCl₃): 1.29(6H, s), 3.12(1H, m), 6.8(2H, m), 7.13(2H, m), 7.52(2H, m), 8.25(1H, m).

Preparation 20
4-Thiophenoxy-2-chloropyridine

The title compound (2.3 g) was prepared by the same procedure as the preparation 1 except for using thiophenol (2.9 g).

¹H NMR δ(CDCl₃): 6.19(3H, m), 7.11(2H, m), 7.23(1H, d), 7.36(1H, s), 8.75(1H, d), 8.75(1H, d).

Preparation 21
4-Anilinyl-6-chloropyridine

The title compound (3.8 g) was prepared by the same procedure as the preparation 4 except for using 2-chloro-4-nitropyridine (3.2 g) and aniline (5.7 g).

¹H NMR δ(CDCl₃): 6.56(2H, m), 6.68(1H, m), 6.96(2H, m), 7.08(2H, m), 8.64(1H, d).

Preparation 22
2-[N-methyl-N-(4-anilinyl)-6-(pyrimidinyl)amino]ethanol

The title compound (1.2 g) was prepared by the same procedure as the preparation 2 except for using 4-Anilinyl-6-chloropyrimidine (1.5 g) and 2-methyl amino ethanol (10 g).

¹H NMR δ(CDCl₃): 3.05(3H, s), 3.68(2H, m), 3.85(2H, m), 6.72(1H, s), 7.30(1H, m), 7.33(2H, m), 7.45(2H, m), 7.65(1H, s), 8.46(1H, s).

Preparation 23
2-[N-methyl-N-(2-(4-phenoxy)pyridinyl)amino]ethanol

A solution of 2-methyl amino ethanol (20 mL) and 4-phenoxy-2-chloropyridine (1.05 g) was stirred at 120° C. for 4 hours and cooled. The resultant was diluted with ethyl acetate (50 mL), washed three times with brine (20 mL, each time) and then twice with water (20 mL, each time), dried (MgSO₄) and filtered. The filtrate was concentrated under reduced pressure. The residue was subjected to chromatography (ethyl acetate/n-hexane=2/3) to obtain the title compound (1.01 g).

¹H NMR δ(CDCl₃): 3.0(3H, s), 3.74(2H, m), 3.85(2H, m), 6.07(1H, s), 6.24(1H, m), 7.09(2H, m), 7.25(2H, m), 7.44(2H, m), 7.94(1H, d).

Preparation 24
2-[N-methyl-N-(6-(4-(4-fluoro)phenoxy)pyrimidinyl)amino]ethanol The title compound (2.1 g) was prepared by the same procedure as the preparation 2 except for using 4-(4-fluoro)phenoxy-6-chloropyrimidine (2.5 g) and 2-methyl amino ethanol (20 mL).

¹H NMR δ(CDCl₃): 3.07(3H, s), 3.78(2H, m), 3.86(2H, m), 5.88(1H, s), 7.11(4H, m), 8.25(1H, s).

Preparation 25
2-[N-methyl-N-(6-(4-(4-chloro)phenoxy)pyrimidinyl)amino]ethanol The title compound (3.15 g) was prepared by the same procedure as the preparation 2 except for using 4-(4-chloro)phenoxy-6-chloropyrimidine (3.2 g) and 2-methyl amino ethanol (30 mL).

¹H NMR δ(CDCl₃): 3.08(3H, s), 3.80(2H, m), 3.88(2H, m), 5.91(1H, s), 7.09(2H, m), 7.37(2H, m), 8.26(1H, s).

Preparation 26
2-[N-methyl-N-(6-(4-(4-methoxy)phenoxy)pyrimidinyl)amino]ethanol The title compound (3.02 g) was prepared by the same procedure as the preparation 2 except for using 4-(4-methoxy)phenoxy-6-chloropyrimidine (3.2 g) and 2-methyl amino ethanol (30 mL).

¹H NMR δ(CDCl₃): 3.05(3H, s), 3.79(2H, m), 3.83(3H, m), 3.87(2H, m), 5.84(1H, s), 6.29(2H, m), 7.06(2H, m), 8.27(1H, s).

Preparation 27
2-[N-methyl-N-(6-(4-(4-ethoxy)phenoxy)pyrimidinyl)amino]ethanol The title compound (930 mg) was prepared by the same procedure as the preparation 2 except for using 4-(4-ethoxy)phenoxy-6-chloropyrimidine (950 mg) and 2-methyl amino ethanol (20 mL).

¹H NMR δ(CDCl₃): 1.35(3H, m), 3.01(3H, s), 3.79(2H, m), 3.81(2H, m), 5.91(1H, s), 6.90(2H, m), 7.13(2H, m), 8.31(1H, s).

Preparation 28
2-[N-methyl-N-(6-(4-(4-isopropoxy)phenoxy)pyrimidinyl)amino]ethanol The title compound (1860 mg) was prepared by the same procedure as the preparation 2 except for using 4-(4-isopropoxy)phenoxy-6-chloropyrimidine (900 mg) and 2-methyl amino ethanol (10 mL).

¹H NMR δ(CDCl₃): 1.37(6H, s), 3.04(3H, s), 3.78(2H, m), 3.85(2H, m), 4.05(1H, s), 5.86(1H, s), 6.92(2H, m), 7.08(2H, m), 8.30(1H, s).

Preparation 29
2-[N-methyl-N-(6-(4-(4-ethyl)phenoxy)pyrimidinyl)amino]ethanol The title compound (1.05 g) was prepared by the same procedure as the preparation 2 except for using 4-(4-ethyl)phenoxy-6-chloropyrimidine (1.1 g) and 2-methyl amino ethanol (20 mL).

¹H NMR δ(CDCl₃): 1.33(2H, m), 3.11(3H, s), 3.73(1H, m), 3.81(2H, m), 3.89(2H, m), 4.22(2H, m), 5.88(1H, s), 7.23(2H, m), 7.31(2H, m), 8.29(1H, s).

Preparation 30
2-[N-methyl-N-(6-(4-(4-methyl)phenoxy)pyrimidinyl) amino]ethanol

The title compound (360 mg) was prepared by the same procedure as the preparation 2 except for using 4-(4-methyl) phenoxy-6-chloropyrimidine (350 mg) and 2-methyl amino ethanol (10 mL).

¹H NMR δ(CDCl₃): 2.40(3H, s), 3.04(3H, s), 3.83(2H, m), 3.88(2H, m), 5.93(1H, s), 7.18(2H, m), 7.38(2H, m), 8.35(1H, s).

Preparation 31
2-[N-methyl-N-(6-(4-(4-isopropyl)phenoxy)pyrimidinyl) amino]ethanol The title compound (1.03 g) was prepared by the same procedure as the preparation 2 except for using 4-(4-isopropyl)phenoxy-6-chloropyrimidine (1.1 g) and 2-methyl amino ethanol (10 mL).

¹H NMR δ(CDCl₃): 1.32(6H, s), 3.01(3H, s), 3.12(1H, m), 3.78(2H, m), 3.89(2H, m), 6.04(1H, s), 7.44(3H, m), 7.68(2H, m), 8.39(1H, s).

Preparation 32
2-[N-methyl-N-(6-(4-(4-phenyl)phenoxy)pyrimidinyl) amino]ethanol

The title compound (920 mg) was prepared by the same procedure as the preparation 2 except for using 4-(4-phenyl) phenoxy-6-chloropyrimidine (870 mg) and 2-methyl amino ethanol (15 mL).

¹H NMR δ(CDCl₃): 3.09(3H, s), 3.81(2H, m), 3.89(2H, m), 5.95(1H, s), 7.21(2H, m), 7.36(1H, m), 7.46(2H, m), 7.63(4H, m), 8.30(1H, s).

Preparation 33
2-[N-methyl-N-(6-(4-thiophenoxy)pyrimidinyl)amino] ethanol

The title compound (1.05 g) was prepared by the same procedure as the preparation 2 except for using 4-(4-thiophenoxy)-6-chloropyrimidine (1.2 g) and 2-methyl amino ethanol (20 mL).

¹H NMR δ(CDCl₃): 3.03(3H, s), 3.79(2H, m), 3.88(2H, m), 6.01(1H, s), 7.43(3H, m), 7.61(2H, m), 8.35(1H, s).

Preparation 34
2-[N-methyl-N-2-(4-(4-fluoro)phenoxy)pyridinyl)amino] ethanol

The title compound (1.1 g) was prepared by the same procedure as the preparation 23 except for using 4-(4-fluoro) phenoxy-2-chloropyridine (1.25 g) and 2-methyl amino ethanol (20 mL).

¹H NMR δ(CDCl₃): 2.98(3H, s), 3.54(2H, m), 3.73(2H, m), 6.01(1H, s), 6.16(1H, m), 7.07(4H, m), 7.97(1H, s).

Preparation 35
2-[N-methyl-N-2-(4-(4-chloro)phenoxy)pyridinyl)amino] ethanol

The title compound (2.1 g) was prepared by the same procedure as the preparation 23 except for using 4-(4-chloro)phenoxy-2-chloropyridine (2.5 g) and 2-methyl amino ethanol (20 mL).

¹H NMR δ(CDCl₃): 2.99(3H, s), 3.51(2H, m), 3.81(2H, m), 5.99(1H, s), 6.20(1H, m), 7.13(4H, m), 7.99(1H, s).

Preparation 36
2-[N-methyl-N-(2-(4-(4-methoxy)phenoxy)pyridinyl) amino]ethanol

The title compound (1.13 g) was prepared by the same procedure as the preparation 23 except for using 4-(4-methoxy)phenoxy-2-chloropyridine (1.15 g) and 2-methyl amino ethanol (15 mL).

¹H NMR δ(CDCl₃): 3.03(3H, s), 3.75(3H, s), 3.49(2H, m), 3.78(2H, m), 6.08(1H, s), 6.19(1H, m), 7.18(4H, m), 7.96(1H, s).

Preparation 37
2-[N-methyl-N-(2-(4-(4-isopropyl)phenoxy)pyridinyl) amino]ethanol The title compound (2.03 g) was prepared by the same procedure as the preparation 23 except for using 4-(4-isopropyl)phenoxy-2-chloropyridine (2.13 g) and 2-methyl amino ethanol (15 mL).

¹H NMR δ(CDCl₃): 1.30(6H, s), 2.98(3H, s), 3.13(2H, m), 3.53(2H, m), 3.91(2H, m), 5.96(1H, s), 6.31(1H, m), 7.03(2H, m), 7.15(2H, m), 8.01(1H, s).

Preparation 38
2-[N-methyl-N-(2-(4-thiophenoxy)pyridinyl)amino]ethanol

The title compound (1.13 g) was prepared by the same procedure as the preparation 23 except for using 4-thiophenoxy-2-chloropyridine (1.18 g) and 2-methyl amino ethanol (18 mL).

¹H NMR δ(CDCl₃): 2.99(3H, s), 3.58(2H, m), 3.91(2H, m), 6.49(1H, d), 6.58(1H, s), 7.04(1H, m), 7.13(4H, m), 8.18(1H, m).

Preparation 39
2-[N-methyl-N-(2-(4-anilinyl)pyridinyl)amino]ethanol

The title compound (1.25 g) was prepared by the same procedure as the preparation 23 except for using 4-anilinyl-6-chloropyridine (1.34 g) and 2-methyl amino ethanol (30 mL).

¹H NMR δ(CDCl₃): 3.01(3H, s), 4.05(2H, m), 4.31(2H, m), 5.91(2H, m), 6.61(2H, m), 6.68(1H, m), 7.08(2H, m), 7.99(1H, d).

Preparation 40
4-[2-(N-methyl-N-(6-(4-anilinyl)pyrimidinyl)amino) ethoxy]benzaldehyde The title compound (980 mg) was prepared by the same procedure as the preparation 3 except for using 2-[N-methyl-N-(6-(4-anilinyl)pyrimidinyl)amino]ethanol (1.34 g) and 4-fluorobenzaldehyde (1.13 g).

¹H NMR δ(CDCl₃): 3.08(3H, s), 4.02(2H, m), 4.27(2H, m), 5.87(1H, s), 6.76(1H, broad s), 7.01(2H, m), 7.16(1H, m), 7.29(2H, m), 7.36(2H, m), 7.84(2H, m), 8.27(1H, s), 9.89(1H, s).

Preparation 41
4-[2-(N-methyl-N-(2-(4-phenoxy)pyridinyl)amino)ethoxy] benzaldehyde The title compound (1 g) was prepared by the same procedure as the preparation 3 except for using 2-[N-methyl-N-(2-(4-phenoxy)pyridinyl)amino]ethanol (1.54 g) and 4-fluorobenzaldehyde (1.13 g).

¹H NMR δ(CDCl₃): 3.09(3H, s), 4.02(2H, m), 4.29(2H, m), 6.09(1H, s), 6.19(1H, m), 7.01(2H, m), 7.09(2H, m), 7.23(1H, m), 7.40(2H, m), 7.84(2H, m), 8.04(1H, s), 9.99(1H, s).

Preparation 42
4-[2-(N-methyl-N-(6-(4-(4-fluoro)phenoxy)pyrimidinyl)amino)ethoxy]benzaldehyde The title compound (570 mg) was prepared by the same procedure as the preparation 3 except for using 2-[N-methyl-N-(6-(4-(4-fluoro)phenoxy)pyrimidinyl)amino]ethanol (920 mg) and 4-fluorobenzaldehyde (800 mg).

$^1$H NMR δ(CDCl$_3$): 3.16(3H, s), 4.07(2H, m), 4.31(2H, m), 5.91(1H, s), 7.01(2H, m), 7.11(5H, m), 7.85(2H, m), 8.31(1H, s), 9.91(1H, s).

Preparation 43
4-[2-(N-methyl-N-(6-(4-(4-chloro)phenoxy)pyrimidinyl)amino)ethoxy]benzaldehyde The title compound (870 mg) was prepared by the same procedure as the preparation 3 except for using 2-[N-methyl-N-(6-(4-(4-chloro)phenoxy)pyrimidinyl)amino]ethanol (1.03 g) and 4-fluorobenzaldehyde (880 mg).

$^1$H NMR δ(CDCl$_3$): 3.17(3H, s), 4.07(2H, m), 4.31(2H, m), 5.93(1H, s), 7.01(2H, m), 7.09(2H, m), 7.37(2H, m), 7.84(2H, m), 8.31(1H, s), 9.90(1H, s).

Preparation 44
4-[2-(N-methyl-N-(6-(4-(4-methoxy)phenoxy)pyrimidinyl)amino)ethoxy]benzaldehyde The title compound (490 mg) was prepared by the same procedure as the preparation 3 except for using 2-[N-methyl-N-(6-(4-(4-methoxy)phenoxy)pyrimidinyl)amino]ethanol (530 mg) and 4-fluorobenzaldehye (430 mg).

$^1$H NMR δ(CDCl$_3$): 3.14(3H, s), 3.83(3H, s), 4.06(2H, m), 4.29(2H, m), 5.86(1H, s), 7.02(6H, m), 7.84(2H, m), 8.32(1H, s), 9.91(1H, s).

Preparation 45
4-[2-(N-methyl-N(6-(4-(4-ethoxy)phenoxy)pyrimidinyl)amino)ethoxy]benzaldehyde The title compound (3.1 g) was prepared by the same procedure as the preparation 3 except for using 2-[N-methyl-N-(6-(4(4-ethoxy)phenoxy)pyrimidinyl)amino]ethanol (3.42 g) and 4-fluorobenzaldehyde (2.94 g).

$^1$H NMR δ(CDCl$_3$): 3.32(3H, m), 3.10(3H, s), 3.85(2H, m), 4.03(2H, m), 4.17(2H, m), 5.75(1H, s), 7.05(6H, m), 7.93(2H, m), 8.41(1H, s), 9.89(1H, s).

Preparation 46
4-[2-(N-methyl-N-(6-(4-(4-isopropoxy)phenoxy)pyrimidinyl)amino)ethoxy]benzaldehyde The title compound (3.42 g) was prepared by the same procedure as the preparation 3 except for using 2-[N-methyl-N-(6-(4-(4-isopropoxy)phenoxy)pyrimidinyl)amino]ethanol (3.65 g) and 4-fluorobenzaldehyde (2.95 g).

$^1$H NMR δ(CDCl$_3$): 1.37(6H, s), 3.11(3H, s), 4.02(3H, m), 4.25(2H, m), 5.83(1H, s), 7.05(6H, m), 7.85(2H, m), 8.35(1H, s), 9.87(1H, s).

Preparation 47
4-[2-(N-methyl-N-(6-(4-(4-ethyl)phenoxy)pyrimidinyl)amino)ethoxy]benzaldehyde The title compound (2.94 g) was prepared by the same procedure as the preparation 3 except for using 2-[N-methyl-N-(6-(4-(4-ethyl)phenoxy)pyrimidinyl)amino]ethanol (3.12 g) and 4-fluorobenzaldehyde (3.01 g).

$^1$H NMR δ(CDCl$_3$): 1.34(3H, m), 3.15(3H, s), 3.75(1H, m), 4.01(4H, m), 4.26(4H, m), 4.26(2H, m), 5.83(1H, s), 7.08(2H, m), 7.15(2H, m), 7.26(2H, m), 7.89(2H, m), 8.35(1H, s), 9.88(1H, s).

Preparation 48
4-[2-(N-methyl-N-6-(4-(4-methyl)phenoxy)pyrimidinyl)amino)ethoxy]benzaldehyde The title compound (1.01 g) was prepared by the same procedure as the preparation 3 except for using 2-[N-methyl-N-(6-(4-(4-methyl)phenoxy)pyrimidinyl)amino]ethanol (1.03 g) and 4-fluorobenzaldehyde (920 mg).

$^1$H NMR δ(CDCl$_3$): 2.41(3H, s), 2.97(3H, s), 3.94(2H, m), 4.24(2H, m), 5.94(1H, s), 7.03(2H, m), 7.23(2H, m), 7.46(2H, m), 7.83(2H, m), 8.31(1H, s), 9.93(1H, s).

Preparation 49
4-[2-(N-methyl-N-(6-(4-(4-isopropyl)phenoxy)pyrimidinyl)amino)ethoxy]benzaldehyde The title compound (1.15 g) was prepared by the same procedure as the preparation 3 except for using 2-[N-methyl-N-(6-(4-(4-isopropyl)phenoxy)pyrimidinyl)amino]ethanol (1.34 g) and 4-fluorobenzaldehyde (1.24 g).

$^1$H NMR δ(CDCl$_3$): 1.29(6H, s), 3.18(3H, s), 3.21(1H, m), 3.99(2H, m), 4.35(2H, m), 5.95(1H, s), 6.95(2H, m), 7.45(3H, m), 7.65(2H, m), 7.84(2H, m), 8.47(1H, s), 9.92(1H, s).

Preparation 50
4-[2-(N-methyl-N-(6-(4-(4-phenyl)phenoxy)pyrimidinyl)amino)ethoxy]benzaldehyde The title compound (897 mg) was prepared by the same procedure as the preparation 3 except for using 2-[N-methyl-N-6-(4-(4-phenyl)phenoxy)pyrimidinyl)amino]ethanol (980 mg) and 4-fluorobenzaldehyde (920 mg).

$^1$H NMR δ(CDCl$_3$): 3.19(3H, s), 4.08(2H, m), 4.31(2H, m), 5.97(1H, s), 7.01(2H, m), 7.21(2H, m), 7.36(1H, m), 7.46(2H, m), 7.61(4H, m), 7.84(2H, m), 8.36(1H, s).

Preparation 51
4-[2-(N-methyl-N-(6-(4-(4-thiophenoxy)pyrimidinyl)amino)ethoxy]benzaldehyde The title compound (1.25 g) was prepared by the same procedure as the preparation 3 except for using 2-[N-methyl-N-(6-(4-thiophenoxy)pyrimidinyl)amino]ethanol (1.4 g) and 4-fluorobenzaldehyde (1.1 g).

$^1$H NMR δ(CDCl$_3$): 2.96(3H, s), 3.96(2H, m), 4.21(2H, m), 5.91(1H, s), 6.96(2H, m), 7.46(3H, m), 7.62(2H, m), 7.85(2H, m), 8.41(1H, s), 9.90(1H, s),

Preparation 52
4-[2-(N-methyl-N-(2-(4-(4-fluoro)phenoxy)pyridinyl)amino)ethoxy]benzaldehyde The title compound (1.12 g) was prepared by the same procedure as the preparation 3 except for using 2-[N-methyl-N-(2-(4-(4-fluoro)phenoxy)pyridinyl)amino]ethanol (1.36 g) and 4-fluorobenzaldehyde (1.25 g).

$^1$H NMR δ(CDCl$_3$): 3.15(3H, s), 4.08(2H, m), 4.33(2H, m), 5.93(1H, s), 6.16(1H, m), 7.01(2H, m), 7.13(5H, m), 7.88(2H, m), 8.33(1H, s), 9.95(1H, s).

Preparation 53
4-[2-(N-methyl-N-(2-(4-(4-chloro)phenoxy)pyridinyl)amino)ethoxy]benzaldehyde The title compound (1.25 g) was prepared by the same procedure as the preparation 3 except for using 2-[N-methyl-N-(2-(4-(4-chloro)phenoxy)pyridinyl)amino]ethanol (1.57 g) and 4-fluorobenzaldehyde (1.25 g).

$^1$H NMR δ(CDCl$_3$): 3.18(3H, s), 4.05(2H, m), 4.30(2H, m), 5.99(1H, s), 6.21(1H, m), 7.01(2H, m), 7.09(2H, m), 7.35(2H, m), 7.88(2H, s), 8.33(1H, s), 9.95(1H, s).

Preparation 54
4-[2-(N-methyl-N-(2-(4-(4-methoxy)phenoxy)pyridinyl)amino)ethoxy]benzaldehyde The title compound (910 mg) was prepared by the same procedure as the preparation 3 except for using 2-[N-methyl-N-(2-(4-(4-methoxy)phenoxy)pyridinyl)amino]ethanol (925 mg) and 4-fluorobenzaldehyde (820 mg).

$^1$H NMR δ(CDCl$_3$): 3.07(3H, s), 3.73(3H, s), 4.05(2H, m), 4.31(2H, m), 6.13(1H, s), 6.19(1H, m), 7.03(2H, m), 7.09(2H, m), 7.25(2H, m), 7.43(2H, m), 7.89(2H, m), 8.01 (1H, s), 9.94(1H, s).

Preparation 55
4-[2-(N-methyl-N-(2-(4-(4-isopropyl)phenoxy)pyridinyl)amino)ethoxy]benzaldehyde The title compound (4.13 g) was prepared by the same procedure as the preparation 3 except for using 2-[N-methyl-N-(2-(4-(4-isopropyl)phenoxy)pyridinyl)amino]ethanol (4.25 g) and 4-fluorobenzaldehyde (3.9 g).

$^1$H NMR δ(CDCl$_3$): 1.32(6H, s), 3.01(3H, s), 3.14(1H, m), 4.01(2H, m), 4.35(2H, m), 6.05(1H, s), 6.16(1H, m), 7.07(2H, m), 7.11(2H, m), 7.21(1H, m), 7.31(4H, m), 8.11 (1H, s), 9.91(1H, s).

Preparation 56
4-[2-(N-methyl-N-2-(4-thiophenoxy)pyridinyl)amino)ethoxy]benzaldehyde The title compound (5.23 g) was prepared by the same procedure as the preparation 3 except for using 2-[N-methyl-N-(2-(4-(4-thiophenoxy)pyridinyl)amino]ethanol (5.74 g) and 4-fluorobenzaldehyde (4.95 g).

$^1$H NMR δ(CDCl$_3$): 3.04(3H, s), 4.03(2H, m), 4.31(2H, m), 6.45(1H, s), 6.54(1H, s), 6.98(4H, m), 7.14(4H, m), 7.75(2H, m), 8.18(1H, d), 9.87(1H, s).

Preparation 57
4-[2-(N-methyl-N-(2-(4-anilinyl)pyridinyl)amino)ethoxy]benzaldehyde The title compound (3.19 g) was prepared by the same procedure as the preparation 3 except for using 2-[N-methyl-N-(2-(4-anilinyl)pyridinyl)amino]ethanol (3.84 g) and 4-fluorobenzaldehyde (3.2 g).

$^1$H NMR δ(CDCl$_3$): 3.01(3H, s), 4.08(2H, m), 4.29(2H, m), 5.88(2H, m), 6.52(3H, m), 7.01(4H, m), 7.70(2H, m), 7.96(1H, d), 9.93(1H, s).

Example 1
5-(4-[2-(N-methyl-N-(6-(4-phenoxy)pyrimidinyl)amino)ethoxy)]benzylidene)-2,4-thiazolidinedione To a solution of 4-[2-(N-methyl-N-(6-(4-phenoxy)pyrimidinyl)amino)ethoxy]benzaldehyde (780 mg) in ethanol (30 mL) were added piperidine (0.3 g) and 2,4-thiazolidinedione (0.4 g). The resultant mixture was stirred under reflux for 24 hours and cooled to 25° C. Then, the obtained resultant was concentrated under reduced pressure, so as to remove solvent. The title compound (720 mg) was obtained by silica gel column chromatography (dichloromethane/methanol=50/1).

$^1$H NMR δ(CDCl$_3$): 3.15(3H, s), 4.04(2H, m), 4.27(2H, m), 5.90(1H, s), 6.99(2H, m), 7.14(2H, m), 7.26(1H, m), 7.44(4H, m), 7.81(1H, s), 8.33(1H, broad s), 8.39(1H, s). m.p.: 185° C.

Example 2
5-(4-[2-(N-methyl-N-(6-(4-anilinyl)pyrimidinyl)amino)ethoxy]benzylidene)-2,4-thiazolidinedione A solution of 2,4-thiazolidinedione (120 mg) and 4-[2-(N-methyl-N-(6-(4-anilinyl)pyrimidinyl)amino)ethoxy] benzaldehyde (280 mg) in a catalytic amount of piperidinium acetate containing toluene (60 mL), was stirred under reflux on a Dean-stark device for 4 hours. The resultant mixture was cooled and filtered. The filtered solid was dried to give the title compound (250 mg).

$^1$H NMR δ(DMSO-d$_6$): 3.04(3H, s), 3.92(2H, m), 4.23 (2H, m), 5.88(1H, s), 6.91(1H, m), 7.12(2H, m), 7.26(2H, m), 7.57(4H, m), 7.74(1H, s), 8.18(1H, s), 9.09(1H, s).

Example 3
5-(4-[2-(N-methyl-N-(2-(4-phenoxy)pyridinyl)amino)ethoxy]benzylidene)-2,4-thiazolidinedione The title compound (300 mg) was prepared by the same procedure as the example 1 except for using the compound (340 mg) obtained from the preparation 41.

$^1$H NMR δ(DMSO-d$_6$): 3.09(3H, s), 4.01(2H, m), 4.25 (2H, m), 6.69(1H, s), 6.19(1H, s), 6.98(2H, m), 7.09(2H, m), 7.22(1H, m), 7.42(4H, m), 7.76(1H, s), 8.05(1H, s). m.p.: 187° C.

Example 4
5-(4-[2-(N-methyl-N-(6-(4-(4-fluoro)phenoxy)pyrimidinyl)amino)ethoxy]benzylidene)-2,4-thiazolidinedione The title compound (270 mg) was prepared by the same procedure as the example 2 except for using the compound (280 mg) obtained from the preparation 42.

$^1$H NMR δ(DMSO-d$_6$): 3.10(3H, s), 3.96(2H, m), 4.25 (2H, m), 6.15(1H, s), 7.21(6H, m), 7.54(2H, m), 7.73(1H, s), 8.18(1H, s). m.p.: 175° C.

Example 5
5-(4-[2-(N-methyl-N-(6-(4-(4-chloro)phenoxy)pyrimidinyl)amino)ethoxy]benzylidene)-2,4-thiazolidinedione The title compound (310 mg) was prepared by the same procedure as the example 1 except for using the compound (340 mg) obtained from the preparation 43.

$^1$H NMR δ(DMSO-d$_6$): 3.11(3H, s), 3.96(2H, m), 4.26 (2H, m), 6.19(1H, s), 7.08(2H, m), 7.18(2H, m), 7.44(2H, m), 7.56(2H, m), 7.73(1H, s), 8.19(1H, s). m.p.: 178° C.

Example 6
5-(4-[2-(N-methyl-N-(6-(4-(4-methoxy)phenoxy)pyrimidinyl)amino)ethoxy]benzylidene)-2,4-thiazolidinedione The title compound (230 mg) was prepared by the same procedure as the example 1 except for using the compound (290 mg) obtained from the preparation 44.

$^1$H NMR δ(DMSO-d$_6$): 3.13(3H, s), 3.83(3H, m), 4.04 (2H, m), 4.26(2H, m), 5.86(1H, s), 7.01(6H, m), 7.46(2H, m), 7.81(1H, s), 8.32(1H, s), 8.68(1H, broad s). m.p.: 180° C.

Example 7
5-(4-[2-(N-methyl-N-(6-(4-4-ethoxy)phenoxy)pyrimidinyl)amino)ethoxy]benzylidene)-2,4-thiazolidinedione The title compound (190 mg) was prepared by the same procedure as the example 1 except for using the compound (210 mg) obtained from the preparation 45.

$^1$H NMR δ(CDCl$_3$): 1.31(3H, m), 3.15(3H, s), 3.97(2H, m), 4.08(2H, m), 4.23(2H, m), 5.74(1H, s), 7.08(6H, m), 7.51(2H, m), 7.85(1H, s), 8.36(1H, s), 8.71(1H, broad s). m.p.: 183° C.

Example 8
5-(4-[2-(N-methyl-N-(6-(4-(4-isopropoxy)phenoxy)pyrimidinyl)amino)ethoxy]benzylidene)-2,4-thiazolidinedione The title compound (210 mg) was prepared by the same procedure as the example 1 except for using the compound (250 mg) obtained from the preparation 46.

$^1$H NMR δ(CDCl$_3$): 1.38(6H, s), 3.18(3H, s), 4.05(3H, m), 4.28(2H, m), 5.83(1H, s), 7.04(6H, m), 7.51(2H, m), 7.79(1H, s), 8.30(1H, s), 8.69(1H, s).

Example 9

5-(4-[2-(N-methyl-N-(6-(4-(4-ethyl)phenoxy)pyrimidinyl)amino)ethoxy]benzylidene)-2,4-thiazolidinedione The title compound (190 mg) was prepared by the same procedure as the example 2 except for using the compound (210 mg) obtained from the preparation 47.

$^1$H NMR δ(DMSO-d$_6$): 1.35(3H, m), 3.15(3H, s), 3.75 (1H, m), 4.05(2H, m), 4.25(2H, m), 4.28(4H, m), 5.75(1H, s), 7.02(6H, m), 7.56(2H, m), 7.80(1H, s), 8.39(1H, s), 8.69(1H, s).

Example 10

5-(4-[2-(N-methyl-N-(6-(4-(4-methyl)phenoxy)pyrimidinyl)amino)ethoxy]benzylidene)-2,4-thiazolidinedione The title compound (180 mg) was prepared by the same procedure as the example 2 except for using the compound (195 mg) obtained from the preparation 48.

$^1$H NMR δ(DMSO-d$_6$): 2.36(3H, s), 3.11(3H, s), 3.94(2H, m), 4.21(2H, m), 5.88(1H, s), 6.93(2H, m), 7.48(4H, m), 7.68(2H, m), 7.88(1H, s), 8.44(1H, s).

Example 11

5-(4-[2-(N-methyl-N-(6-(4-(4-isopropyl)phenoxy)pyrimidinyl)amino)ethoxy]benzylidene-2,4-thiazolidinedione The title compound (210 mg) was prepared by the same procedure as the example 2 except for using the compound (250 mg) obtained from the preparation 49.

$^1$H NMR δ(DMSO-d$_6$): 1.31(6H, s), 2.99(3H, s), 3.99(2H, m), 4.21(2H, m), 5.93(1H, s), 6.95(2H, m), 7.44(4H, m), 7.65(2H, m), 7.75(1H, s), 8.28(1H, s). m.p.: 187° C.

Example 12

5-(4-[2-(N-methyl-N-(6-(4-(4-phenyl)phenoxy)pyrimidinyl)amino)ethoxy]benzylidene)-2,4-thiazolidinedione The title compound (410 mg) was prepared by the same procedure as the example 2 except for using the compound (440 mg) obtained from the preparation 50.

$^1$H NMR δ(CDCl$_3$): 3.10(3H, s), 3.99(2H, m), 4.23(2H, m), 5.87(1H, s), 6.95(2H, m), 7.16(2H, m), 7.39(1H, m), 7.41(4H, m), 7.56(4H, m), 7.72(1H, s), 8.26(1H, s).

Example 13

5-(4-[2-(N-methyl-N-(6-(4-thiophenoxy)pyrimidinyl)amino)ethoxy)]benzylidene)-2,4-thiazolidinedione The title compound (340 mg) was prepared by the same procedure as the example 2 except for using the compound (390 mg) obtained from the preparation 51.

$^1$H NMR δ(CDCl$_3$): 2.98(3H, s), 3.97(2H, m), 4.20(2H, m), 5.91(1H, s), 6.94(2H, m), 7.46(4H, m), 7.62(2H, m), 7.81(1H, s), 8.41(1H, s).

Example 14

5-(4-[2-(N-methyl-N-(2-(4-(4-fluoro)phenoxy)pyridinyl)amino)ethoxy]benzylidene)-2,4-thiazolidinedione The title compound (320 mg) was prepared by the same procedure as the example 2 except for using the compound (380 mg) obtained from the preparation 52.

$^1$H NMR δ(DMSO-d$_6$): 3.11(3H, s), 4.05(2H, m), 4.28 (2H, m), 5.98(1H, s), 6.14(1H, m), 7.05(2H, m), 7.15(5H, m), 7.78(1H, s), 7.88(2H, m), 8.35(1H, s).

Example 15

5-(4-[2-(N-methyl-N-(2-(4-(4-chloro)phenoxy)pyridinyl)amino)ethoxy]benzylidene)-2,4-thiazolidinedione The title compound (280 mg) was prepared by the same procedure as the example 2 except for using the compound (320 mg) obtained from the preparation 53.

$^1$H NMR δ(DMSO-d$_6$): 3.05(3H, s), 4.05(2H, m), 4.29 (2H, m), 5.95(1H, s), 6.19(1H, m), 7.03(2H, m), 7.11(2H, m), 7.35(2H, m), 7.75(1H, s), 7.89(2H, m), 8.31(1H, s).

Example 16

5-(4-[2-(N-methyl-N-(2-(4-(4-methoxy)phenoxy)pyridinyl)amino)ethoxy]benzylidene)-2,4-thiazolidinedione The title compound (510 mg) was prepared by the same procedure as the example 1 except for using the compound (540 mg) obtained from the preparation 54.

$^1$H NMR δ(DMSO-d$_6$): 3.07(3H, s), 3.75(3H, s), 4.03(2H, m), 4.27(2H, m), 6.67(1H, s), 6.18(1H, s), 6.97(2H, m), 7.08(2H, m), 7.23(1H, m), 7.44(4H, m), 7.74(1H, s), 8.12 (1H, s).

Example 17

5-(4-[2-(N-methyl-N-(2-(4-(4-isopropyl)phenoxy)pyridinyl)amino)ethoxy]benzylidene)-2,4-thiazolidinedione The title compound (610 mg) was prepared by the same procedure as the example 2 except for using the compound (670 mg) obtained from the preparation 55.

$^1$H NMR δ(DMSO-d$_6$): 1.33(6H, s), 3.01(3H, s), 3.13(1H, m), 3.99(2H, m), 4.29(2H, m), 6.10(1H, m), 6.21(1H, m), 6.96(2H, m), 7.10(2H, m), 7.41(4H, m), 7.73(1H, s), 8.07 (1H, s).

Example 18

5-(4-[2-(N-methyl-N-(2-(4-thiophenoxy)pyridinyl)amino)ethoxy]benzylidene)-2,4-thiazolidinedione The title compound (220 mg) was prepared by the same procedure as the example 1 except for using the compound (240 mg) obtained from the preparation 56.

$^1$H NMR δ(DMSO-d$_6$): 2.97(3H, s), 3.98(2H, m), 4.24 (2H, m), 6.01(1H, s), 6.17(1H, s), 6.89(2H, m), 7.09(2H, m), 7.21(1H, m), 7.45(4H, m), 7.71(1H, s), 8.15(1H, s).

Example 19

5-(4-[2-(N-methyl-N-(2-(4-anilinyl)pyridinyl)amino)ethoxy]benzylidene)-2,4-thiazolidinedione The title compound (330 mg) was prepared by the same procedure as the example 1 except for using the compound (390 mg) obtained from the preparation 57.

$^1$H NMR δ(DMSO-d$_6$): 2.99(3H, s), 4.03(2H, m), 4.29 (2H, m), 5.89(2H, m), 6.46(2H, m), 6.68(3H, m), 7.03(2H, m), 7.19(2H, m), 7.73(1H, s), 7.98(1H, d).

Example 20

5-(4-[2-(N-methyl-N-(6-(4-phenoxy)pyrimidinyl)amino)ethoxy]benzyl)-2,4-thiazolidinedione A solution of 5-(4-[2-(N-methyl-N-(6-(4-phenoxy)pyrimidinyl)amino)ethoxy]benzylidene)-2,4-thiazolidinedione (1.5 g) in dimethyl formamide (100 mL) was stirred under hydrogen atmosphere (1 atm) in the presence of 20% palladium hydroxide on charcoal (1.5 g) for 24 hours. The resultant was filtered through a diatomaceous earth filter, and the filtrate was concentrated under reduced pressure. The title compound (1.1 g) was obtained by silica gel column chromatography (dichloromethane/methanol= 50/1).

$^1$H NMR δ(CDCl$_3$): 3.11(1H, m), 3.15(3H, s), 3.45(1H, m), 4.02(2H, m), 4.15(2H, m), 4.53(1H, m), 5.91(1H, s), 6.83(2H, s), 7.15(4H, m), 7.24(1H, m), 7.45(2H, m), 8.07 (1H, broad s), 8.33(1H, s). m.p.: 145° C.

Example 21
5-(4-[2(N-methyl-N-(6-(4-anilinyl)pyrimidinyl)amino) ethoxy]benzyl)-2,4-thiazolidinedione The title compound (950 mg) was prepared by the same procedure as the example 20 except for using the compound (1.1 g) obtained from the example 2.

$^1$H NMR δ(DMSO-d$_6$): 3.04(3H, s), 3.28(2H, m), 3.87 (2H, m), 4.10(2H, m), 4.81(1H, m), 5.87(1H, s), 6.87(2H, m), 7.15(2H, m), 7.26(3H, m), 7.57(2H, m), 8.17(1H, s), 9.03(1H, s).

Example 22
5-(4-[2-(N-methyl-N-(2-(4-phenoxy)pyridinyl)amino) ethoxy]benzyl)-2,4-thiazolidinedione The title compound (900 mg) was prepared by the same procedure as the example 20 except for using the compound (930 mg) obtained from the example 3.

$^1$H NMR δ(CDCl$_3$): 3.08(3H, s), 3.12(1H, m), 3.45(1H, m), 3.96(2H, m), 4.14(2H, m), 4.51(1H, m), 6.08(1H, s), 6.17(1H, s), 6.83(2H, m), 7.11(4H, m), 7.23(1H, m), 7.42 (2H, m), 8.04(1H, s). m.p.: 152° C.

Example 23
5-(4-[2-(N-methyl-N-(6-(4-(4-fluoro)phenoxy)pyrimidinyl) amino)ethoxy]benzyl)-2,4-thiazolidinedione The title compound (1.1 g) was prepared by the same procedure as the example 20 except for using the compound (1.4 g) obtained from the example 4.

$^1$H NMR δ(DMSO-d$_6$): 3.05(3H, s), 3.13(1H, m), 3.43 (1H, m), 3.98(2H, m), 4.28(2H, m), 4.58(1H, m), 6.13(1H, s), 7.23(6H, m), 7.57(2H, m), 8.19(1H, s). m.p.: 143° C.

Example 24
5-(4-[2-(N-methyl-N-(6-(4-(4-chloro)phenoxy)pyrimidinyl) amino)ethoxy]benzyl)-2,4-thiazolidinedione The title compound (1 g) was prepared by the same procedure as the example 20 except for using the compound (1.2 g) obtained from the example 5.

$^1$H NMR δ(DMSO-d$_6$): 3.13(3H, s), 3.15(1H, m), 3.41 (1H, m), 3.99(2H, m), 4.31(2H, m), 4.52(1H, m), 6.14(1H, s), 7.09(2H, m), 7.18(2H, m), 7.45(2H, m), 7.58(2H, m), 8.21(1H, s). m.p.: 151° C.

Example 25
5-(4-[2-(N-methyl-N-(6-(4-(4-methoxy)phenoxy) pyrimidinyl)amino)ethoxy]benzyl)-2,4-thiazolidinedione The title compound (1.1 g) was prepared by the same procedure as the example 20 except for using the compound (1.3 g) obtained from the example 6.

$^1$H NMR (CDCl$_3$): 3.16(3H, s), 3.46(1H, m), 3.83(3H, s), 4.01(2H, m), 4.19(2H, m), 4.51(1H, m), 5.85(1H, s), 7.02 (8H, m), 8.31(1H, s), 8.33(1H, s), m.p.: 148° C.

Example 26
5-(4-[2-(N-methyl-N-(6-(4-(4-ethoxy)phenoxy) pyrimidinyl)amino)ethoxy]benzyl)-2,4-thiazolidinedione The title compound (1 g) was prepared by the same procedure as the example 20 except for using the compound (1.5 g) obtained from the example 7.

$^1$H NMR δ(CDCl$_3$): 1.34(3H, m), 3.13(3H, s), 3.41(1H, m), 3.81(2H, m), 4.08(2H, m), 4.21(2H, m), 4.53(1H, m), 5.75(1H, s), 7.03(8H, m), 8.35(1H, s), 8.37(1H, s), 8.34(1H, broad s).

Example 27
5-(4-[2-(N-methyl-N-(6-(4-(4-isopropoxy)phenoxy) pyrimidinyl)amino)ethoxy]benzyl)-2,4-thiazolidinedione The title compound (1.3 g) was prepared by the same procedure as the example 20 except for using the compound (1.8 g) obtained from the example 8.

$^1$H NMR δ(CDCl$_3$): 1.38(6H, s), 3.15(3H, s), 3.46(1H, m), 3.82(1H, m), 4.04(1H, m), 4.09(2H, m), 4.25(2H, m), 4.59(1H, m), 5.79(1H, s), 7.05(8H, m), 8.37(1H, s), 8.34 (1H, broad s).

Example 28
5-(4-[2-(N-methyl-N-(6-(4-(4-ethyl)phenoxy)pyrimidinyl) amino)ethoxy]benzyl)-2,4-thiazolidinedione The title compound (1.1 g) was prepared by the same procedure as the example 20 except for using the compound (1.4 g) obtained from the example 9.

$^1$H NMR δ(DMSO-d$_6$): 1.38(3H, m), 3.17(3H, s), 3.47 (2H, m), 3.75(1H, m), 4.02(2H, m), 4.18(4H, m), 4.25(2H, m), 4.54(1H, m), 5.78(1H, s), 7.04(8H, m), 8.34(1H, s), 8.38(1H, s).

Example 29
5-(4-[2-(N-methyl-N-(6-(4-(4-methyl)phenoxy) pyrimidinyl)amino)ethoxy]benzyl)-2,4-thiazolidinedione The title compound (1.2 g) was prepared by the same procedure as the example 20 except for using the compound (1.5 g) obtained from the example 10.

$^1$H NMR δ(DMSO-d$_6$): 2.38(3H, s), 3.11(1H, m), 3.18 (3H, s), 3.44(1H, m), 4.08(2H, m), 4.21(2H, m), 4.58(1H, m), 5.91(1H, s), 6.89(2H, m), 7.13(2H, m), 7.43(2H, m), 7.63(2H, m), 8.31(1H, s), 8.78(1H, s).

Example 30
5-(4-[2-(N-methyl-N-(6-(4-(4-isopropyl)phenoxy) pyrimidinyl)amino)ethoxy]benzyl)-2,4-thiazolidinedione The title compound (1.3 g) was prepared by the same procedure as the example 20 except for using the compound (1.4 g) obtained from the example 11.

$^1$H NMR δ(DMSO-d$_6$): 1.28(6H, s), 3.10(1H, m), 3.18 (3H, s), 3.44(1H, m), 4.09(2H, m), 4.21(2H, m), 4.53(1H, m), 5.84(1H, s), 6.88(2H, m), 7.15(2H, m), 7.23(2H, m), 7.48(2H, m), 8.31(1H, s), 8.75(1H, s). m.p.: 153° C.

Example 31
5-(4-[2-(N-methyl-N-(6-(4-4-phenyl)phenoxy)pyrimidinyl) amino)ethoxy]benzyl)-2,4-thiazolidinedione The title compound (1.25 g) was prepared by the same procedure as the example 20 except for using the compound (1.5 g) obtained from the example 12.

$^1$H NMR δ(DMSO-d$_6$): 3.12(1H, m), 3.16(3H, s), 3.42 (1H, m), 4.02(2H, m), 4.19(2H, m), 4.51(1H, m), 5.95(1H, s), 6.83(2H, m), 7.13(2H, m), 7.21(2H, m), 7.36(1H, m), 7.45(2H, m), 7.61(4H, m), 8.34(1H, s), 8.71(1H, broad s).

Example 32
5-(4-[2(N-methyl-N-(6-(4-thiophenoxy)pyrimidinyl)amino) ethoxy]benzyl)-2,4-thiazolidinedione The title compound (1.6 g) was prepared by the same procedure as the example 20 except for using the compound (1.9 g) obtained from the example 13.

$^1$H NMR δ(DMSO-d$_6$): 2.99(3H, s), 3.13(1H, m), 3.45 (1H, m), 3.99(2H, m), 4.21(2H, m), 4.58(1H, m), 5.93(1H, s), 6.95(2H, m), 7.48(4H, m), 7.63(2H, m), 8.41(1H, s).

Example 33
5-(4-[2-(N-methyl-N-(2-(4-(4-fluoro)phenoxy)pyridinyl) amino)ethoxy]benzyl)-2,4-thiazolidinedione The title compound (1.1 g) was prepared by the same procedure as the example 20 except for using the compound (1.2 g) obtained from the example 14.

$^1$H NMR δ(DMSO-d$_6$): 3.08(3H, s), 3.11(1H, m), 3.40 (1H, m), 4.08(2H, m), 4.33(2H, m), 4.54(1H, m), 5.96(1H, s), 6.15(1H, m), 7.06(2H, m), 7.17(5H, m), m), 7.84(2H, m), 8.39(1H, s).

Example 34
5-(4-[2-(N-methyl-N-(2-(4-(4-chloro)phenoxy)pyridinyl)amino)ethoxy]benzyl)-2,4-thiazolidinedione The title compound (1.25 g) was prepared by the same procedure as the example 20 except for using the compound (1.3 g) obtained from the example 15.

$^1$H NMR δ(DMSO-$d_6$): 2.99(3H, s), 3.15(1H, m), 3.40 (1H, m), 4.01(2H, m), 4.33(2H, m), 4.56(1H, m), 5.97(1H, s), 6.14(1H, m), 7.05(2H, m), 7.13(2H, m), 7.34(2H, m), 7.87(2H, m), 8.32(1H, s).

Example 35
5-(4-[2-(N-methyl-N-(2-(4-(4-methoxy)phenoxy)pyridinyl)amino)ethoxy]benzyl)-2,4-thiazolidinedione The title compound (1.4 g) was prepared by the same procedure as the example 20 except for using the compound (1.5 g) obtained from the example 16.

$^1$H NMR δ(DMSO-$d_6$): 3.04(3H, s), 3.13(1H, m), 3.47 (1H, m), 3.78(3H, s), 3.98(2H, m), 4.17(2H, m), 4.54(1H, m), 6.04(1H, s), 6.19(1H, s), 6.87(2H, m), 7.17(4H, m), 7.45(2H, m), 8.12(1H, s).

Example 36
5-(4-[2-(N-methyl-N-2-(4-(4-isopropyl)pyridinyl)amino)ethoxy]benzyl)-2,4-thiazolidinedione The title compound (1.6 g) was prepared by the same procedure as the example 20 except for using the compound (1.7 g) obtained from the example 17.

$^1$H NMR δ(DMSO-$d_6$): 1.33(6H, s), 3.01(3H, s), 3.15(2H, m), 3.47(1H, m), 3.99(2H, m), 4.19(2H, m), 4.59(1H, m), 6.09(1H, s), 6.19(1H, s), 6.88(2H, m), 7.15(4H, m), 7.26 (1H, m), 7.41(1H, m), 8.15(1H, s).

Example 37
5-(4-[2-(N-methyl-N-(2-(4-thiophenoxy)pyridinyl)amino)ethoxy]benzyl)-2,4-thiazolidinedione The title compound (1.7 g) was prepared by the same procedure as the example 20 except for using the compound (1.8 g) obtained from the example 18.

$^1$H NMR δ(DMSO-$d_6$): 2.99(3H, s), 3.15(1H, m), 3.47 (1H, m), 4.03(2H, m), 4.25(2H, m), 4.55(1H, m), 6.01(1H, s), 6.21(1H, s), 6.94(2H, m), 7.47(4H, m), 7.62(2H, m), 7.81(1H, s), 8.19(1H, s).

Example 38
5-(4-[2-(N-methyl-N-(2-(4-anilinyl)pyridinyl)amino)ethoxy]benzyl)-2,4-thiazolidinedione The title compound (1.0 g) was prepared by the same procedure as the example 20 except for using the compound (1.5 g) obtained from the example 19.

$^1$H NMR δ(DMSO-$d_6$): 3.04(3H, s), 3.18(1H, m), 3.45 (1H, m), 4.01(2H, m), 4.28(2H, m), 4.58(1H, m), 5.94(2H, m), 6.48(2H, m), 6.69(3H, m), 7.03(4H, m), 7.99(1H, d), 9.99(1H, broad s).

Experiments: Measurements of the Efficacies of Test Compounds 1) 2-Deoxy-D-[2,6-3H] glucose uptake assay (in differentiated 3T3-L1 cell)

Undifferentiated adipocyte 3T3-L1 cells were inoculated in a 24-well plate and cultivated in a $CO_2$ incubator at 37° C. To induce differentiation of the undifferentiated adipocytes, the cells were then incubated in a differentiation medium. After adding a certain concentration of each of the test compounds to the medium, the cells were again incubated for 24 hours. After removing the medium, the cells were washed with phosphate buffer, and 0.5 nM of insulin in phosphate buffer was added to the washed cells, followed by incubation for 40 minutes. Then, 0.5 uCi of 2-deoxy-D-[2, 6-3H] glucose per well was again added to the cells, which were let stand for 4 minutes. Then, the cells were washed with phosphate buffer, and cell lysis buffer was added, so as to dissolve the cell membranes. The cell sample was placed into a liquid scintillation cocktail solution. The radioactivity of the sample was counted by a liquid scintillation counter. Based on the obtained results, the concentrations of the test compounds which resulted in 50% of maximum enhancement of insulin activation, were determined ($EC_{50}$, nM). The results are presented in Table 1.

2) Triglyceride accumulation assay (in 3T3-L1 cells)

Undifferentiated adipocyte 3T3-L1 cells were inoculated in a 24-well plate and cultivated in a $CO_2$ incubator at 37° C. To induce differentiation of the undifferentiated adipocytes, the cells were then incubated in a differentiation medium for 48 hours. After adding a certain concentration of each of the test compounds to the differentiation medium, the cells were again incubated for 4 days. Then, the final cell sample was placed into 200 μl of 2-propanol. The amount of triglyceride in the cells were measured by Triglyceride Kit [YEONGDONG PHARMACEUTICAL CO. LTD., Korea] commercially available. Based on the obtained results, the concentration of the test compounds which resulted in 50% of maximum enhancement of rosiglitazone activation, were determined ($EC_{50}$, nM). The results are presented in Table 1.

3) Cytotoxicity assay in primary cultured rat hepatocytes

Hepatocytes isolated from rat were inoculated in a collagen-coated 24 well plate and was incubated in a $CO_2$ incubator at 37° C. for 24 hours. Then, a certain concentration of each of the test compounds was added, and the cells were again incubated for 24 hours. The cells were then incubated in a 0.4% neutral red containing medium for 4 hours and washed once with phosphate buffer. 0.5 ml of a solution of 1% acetic acid-50% ethanol was added to the cells, which were let stand. 200 ul of the cell sample was taken and absorbance was measured at 570 nm. The cytotoxicity assay performed on hepatocytes was measured as 25% toxic concentration ($TC_{25}$, uM). Then, the safety index, i.e. the $TC_{25}$ value in the cytotoxicity assay in hepatocyte/the $EC_{50}$ value in the triglyceride accumulation assay, was calculated. The results are presented in Table 1.

TABLE 1

| Test compound | 2-deoxyglucose uptake ($EC_{50}$ nM) | Triglyceride accumulation ($EC_{50}$ nM) | Cytotoxicity in hepatocyte ($TC_{25}$ uM) | Safety index ($TC_{25}$ nM/ $EC_{50}$ nM) |
|---|---|---|---|---|
| Ex. 24 | 0.2 | 0.1 | 75 | 750000 |
| Ex. 25 | 0.2 | 0.11 | 80 | 727272 |
| Ex. 22 | 1.8 | 0.54 | 74 | 137037 |
| Ex. 23 | 2.4 | 0.81 | 71 | 87654 |
| Ex. 20 | 7.5 | 2.7 | 80 | 29630 |
| Ex. 37 | 2.8 | 1.2 | 95 | 79167 |
| Ex. 34 | 4.0 | 1.5 | 73 | 48667 |
| Ex. 28 | 5.2 | 2.1 | 85 | 40476 |
| Ex. 32 | 5.9 | 3.2 | 89 | 27813 |
| Ex. 38 | 10.5 | 5.5 | 71 | 12909 |
| Ex. 33 | 8.9 | 5.6 | 99 | 17679 |
| Ex. 26 | 14.4 | 7.7 | 95 | 12338 |
| Ex. 30 | 13.3 | 6.5 | 72 | 11077 |
| Ex. 21 | 12.8 | 7.5 | 81 | 10800 |
| Ex. 35 | 19.3 | 9.6 | 96 | 10000 |
| Ex. 31 | 20.5 | 12.5 | 73 | 5840 |
| Ex. 36 | 20.9 | 16.3 | 76 | 4663 |
| Ex. 27 | 35.5 | 21.7 | 78 | 3594 |
| Ex. 19 | 48.2 | 20.1 | 81 | 4030 |
| Ex. 1 | 58 | 38 | 98 | 2578 |
| Ex. 5 | 45 | 35 | 93 | 2657 |
| Ex. 9 | 55.2 | 29.9 | 90 | 3010 |

TABLE 1-continued

| Test compound | 2-deoxyglucose uptake (EC$_{50}$ nM) | Triglyceride accumulation (EC$_{50}$ nM) | Cytotoxicity in hepatocyte (TC$_{25}$ uM) | Safety index (TC$_{25}$ nM/ EC$_{50}$ nM) |
|---|---|---|---|---|
| Ex. 12 | 49.5 | 46.8 | 85 | 1816 |
| Rosiglitazone | 75.0 | 47 | 70 | 1489 |

As can be seen from Table 1, the compounds of the present invention are 1.3 to 375 times higher in terms of the uptake of 2-deoxy-D[2,6-3H] glucose by 3T3-L1 cells, and 1.0 to 470 times higher in terms of triglyceride accumulation, than the rosiglitazone. Furthermore, the compounds of the present invention are lower in terms of the cytotoxicity to hepatocytes and 1.2 to 504 times more excellent in terms of the safety index, than the rosiglitazone.

4) Blood glucose- and blood lipid-lowering action in mice with diabetes

Male mice with diabetes (KK/Ay: 10 weeks old, 5 animals/group) were housed and given free access to water and food. The animals received a daily oral administration of the test compounds for 5 days. After the last dose, a blood sample was drawn via the orbital sinus.

The plasma was analyzed for blood glucose content using the Glucose-E kit (YEONGDONG PHARMACEUTICAL CO. LTD., Korea), and for triglyceride content using the Triglyceride kit (YEONGDONG PHARMACEUTICAL CO. LTD., Korea). Based on the dose-response graph for blood glucose and triglyceride lowering activity, ED$_{25}$ (mg/kg), the dose of the test compound which reduces the blood glucose and triglyceride levels by 25%, was calculated. The results are presented in Table 2.

TABLE 2

| Test compound | Blood glucose (ED$_{25}$) | Triglyceride (ED$_{25}$) |
|---|---|---|
| Ex. 25 | 0.15 | 0.5 |
| Ex. 24 | 0.18 | 0.6 |
| Ex. 20 | 0.22 | 1.2 |
| Ex. 37 | 0.22 | 1.4 |
| Ex. 23 | 0.25 | 2.2 |
| Ex. 22 | 0.7 | 3.9 |
| Ex. 27 | 0.8 | 4.5 |
| Ex. 26 | 0.8 | 4.3 |
| Ex. 33 | 1.1 | 6.5 |
| Ex. 38 | 1.5 | 7.8 |
| Ex. 32 | 1.5 | 12.3 |
| Ex. 28 | 1.8 | 16.9 |
| Ex. 34 | 1.9 | 5.6 |
| Ex. 30 | 2.1 | 21.2 |
| Ex. 35 | 2.5 | 9.1 |
| Ex. 21 | 2.6 | 6.2 |
| Ex. 31 | 3.2 | 12.6 |
| Ex. 36 | 3.5 | 14.9 |
| Ex. 19 | 3.8 | 15.6 |
| Ex. 1 | 4.0 | 30 |
| Ex. 5 | 4.0 | 28 |
| Ex. 9 | 4.1 | 29 |
| Ex. 12 | 4.1 | 25 |
| Rosiglitazone | 4.1 | More than 30 |

As can be seen from the Table 2, the compounds of the present invention exhibited 1.0 to 27 times better blood sugar lowering activity, and 1.0 to 60 times better blood lipid lowering activity, than the rosiglitazone, in mice with diabetes.

Industrial Applicability

As apparent from the above description, the thiazolidinedione derivative or pharmaceutically acceptable salt thereof of the present invention exhibits strong blood sugar- and blood lipid-lowering activities, and, a half life thereof is also noticeably prolonged, as compared with the rosiglitazone. Furthermore, in the thiazolidinedione derivative of the present invention and the pharmaceutical composition containing the same, liver toxicity, a common side effect encountered with this type of compound drug, is not found.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A thiazolidinedione compound, represented in formula (1):

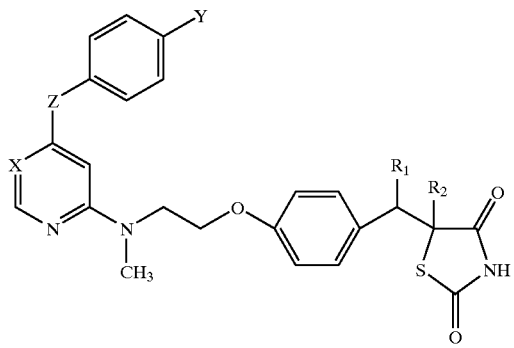

Formula (1)

wherein:
X represents a carbon or nitrogen atom; Y represents a hydrogen atom, an alkyl group, an alkoxy group, a halogen, or an aryl group; Z represents NH, an oxygen, or sulfur atom; and R$_1$ and R$_2$ each represent a hydrogen atom, or R$_1$ and R$_2$ together form a bond,
a pharmaceutically acceptable salt thereof, or a pharmaceutically acceptable solvate thereof.

2. The thiazolidinedione compound as set forth in claim 1, wherein Y represents a hydrogen atom, a C$_1$–C$_4$ alkyl group, a C$_1$–C$_3$ alkoxy group, chlorine, fluorine or a phenyl group.

3. The thiazolidinedione compound as set forth in claim 1, which is selected from the group consisting of:

5-(4-[2-(N-methyl-N-(6-(4-phenoxy)pyrimidinyl)amino)ethoxy]benzylidene)-2,4-thiazolidinedione;

5-(4-[2-(N-methyl-N-(6-(4-anilinyl)pyrimidinyl)amino)ethoxy]benzylidene)-2,4-thiazolidinedione;

5-(4-(2-(N-methyl-N-(2-(4-phenoxy)pyridinyl)amino)ethoxy]benzylidene)-2,4-thiazolidinedione;

5-(4-[2-(N-methyl-N-(6-(4-(4-fluoro)phenoxy)pyrimidinyl)amino)ethoxy]benzylidene)-2,4-thiazolidinedione;

5-(4-[2-(N-methyl-N-(6-(4-(4-chloro)phenoxy)pyrimidinyl)amino)ethoxy]benzylidene)-2,4-thiazolidinedione;

5-(4-[2-(N-methyl-N-(6-(4-(4-methoxy)phenoxy)pyrimidinyl)amino)ethoxy]benzylidene)-2,4-thiazolidinedione;

5-(4-[2-(N-methyl-N-(6-(4-(4-ethoxy)phenoxy)pyrimidinyl)amino)ethoxy]benzylidene)-2,4-thiazolidinedione;

5-(4-[2-(N-methyl-N-(6-(4-(4-isopropoxy)phenoxy)pyrimidinyl)amino)ethoxy]benzylidene)-2,4-thiazolidinedione;

5-(4-[2-(N-methyl-N-(6-(4-(4-methyl)phenoxy)pyrimidinyl)amino)ethoxy]benzylidene)-2,4-thiazolidinedione;

5-(4-[2-(N-methyl-N-(6-(4-(4-ethyl)phenoxy)pyrimidinyl)amino)ethoxy)]benzylidene)-2,4-thiazolidinedione;

5-(4-[2-(N-methyl-N-(6-(4-(4-isopropyl)phenoxy)pyrimidinyl)amino)ethoxy]benzylidene)-2,4-thiazolidinedione;

5-(4-[2-(N-methyl-N-(6-(4-(4-phenyl)phenoxy)pyrimidinyl)amino)ethoxy]benzylidene)-2,4-thiazolidinedione;

5-(4-[2-(N-methyl-N-(6-(4-thiophenoxy)pyrimidinyl)amino)ethoxy]benzylidene)-2,4-thiazolidinedione;

5-(4-[2-(N-methyl-N-(2-(4-(4-methoxy)phenoxy)pyridinyl)amino)ethoxy]benzylidene)-2,4-thiazolidinedione;

5-(4-[2-(N-methyl-N-(2-(4-(4-isopropyl)phenoxy)pyridinyl)amino)ethoxy]benzylidene)-2,4-thiazolidinedione;

5-(4-[2-(N-methyl-N-(2-(4-(4-fluoro)phenoxy)pyridinyl)amino)ethoxy]benzylidene)-2,4-thiazolidinedione;

5-(4-[2-(N-methyl-N-(2-(4-(4-chloro)phenoxy)pyridinyl)amino)ethoxy]benzylidene)-2,4-thiazolidinedione;

5-(4-[2-(N-methyl-N-(2-(4-thiophenoxy)pyridinyl)amino)ethoxy]benzylidene)-2,4-thiazolidinedione;

5-(4-[2-(N-methyl-N-(2-(4-anilinyl)pyridinyl)amino)ethoxy]benzylidene)-2,4-thiazolidinedione;

5-(4-[2-(N-methyl-N-(6-(4-phenoxy)pyrimidinyl)amino)ethoxy]benzyl)-2,4-thiazolidinedione;

5-(4-[2-(N-methyl-N-(6-(4-anilinyl)pyrimidinyl)amino)ethoxy]benzyl)-2,4-thiazolidinedione;

5-(4-[2-(N-methyl-N-(2-(4-phenoxy)pyridinyl)amino)ethoxy]benzyl)-2,4-thiazolidinedione;

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]benzyl)-2,4-thiazolidinedione;

5-(4-[2-(N-methyl-N-(6-(4-(4-ethoxy)phenoxy)pyrimidinyl)amino)ethoxy]benzyl)-2,4-thiazolidinedione;

5-(4-[2-(N-methyl-N-(6-(4-(4-isopropoxy)phenoxy)pyrimidinyl)amino)ethoxy]benzyl)-2,4-thiazolidinedione;

5-(4-[2-(N-methyl-N-(6(4-(4-methyl)phenoxy)pyrimidinyl)amino)ethoxy]benzyl)-2,4-thiazolidinedione;

5-(4-[2-(N-methyl-N-(6-(4-(4-ethyl)phenoxy)pyrimidinyl)amino)ethoxy]benzyl)-2,4-thiazolidinedione;

5-(4-[2-(N-methyl-N-(6-(4-(4-isopropyl)phenoxy)pyrimidinyl)amino)ethoxy]benzyl)-2,4-thiazolidinedione;

5-(4-[2-(N-methyl-N-(6-(4-(4-phenyl)phenoxy)pyrimidinyl)amino)ethoxy]benzyl)-2,4-thiazolidinedione;

5-(4-[2-(N-methyl-N-(6-(4-thiophenoxy)pyrimidinyl)amino)ethoxy]benzyl)-2,4-thiazolidinedione;

5-(4-[2-(N-methyl-N-(2-(4-(4-fluoro)phenoxy)pyridinyl)amino)ethoxy]benzyl)-2,4-thiazolidinedione;

5-(4-[2-(N-methyl-N-(2-(4-(4-chloro)phenoxy)pyridinyl)amino)ethoxy]benzyl)-2,4-thiazolidinedione;

5-(4-[2-(N-methyl-N-(2-(4-(4-methoxy)phenoxy)pyridinyl)amino)ethoxy]benzyl)-2,4-thiazolidinedione;

5-(4-[2-(N-methyl-N-(2-(4-(4-isopropyl)phenoxy)pyridinyl)amino)ethoxy]benzyl)-2,4-thiazolidinedione;

5-(4-[2-(N-methyl-N-(2-(4-thiophenoxy)pyridinyl)amino)ethoxy]benzyl)-2,4-thiazolidinedione; and 5-(4-[2-(N-methyl-N-(2-(4-anilinyl)pyridinyl)amino)ethoxy]benzyl)-2,4-thiazolidinedione.

4. The thiazolidinedione compound as set forth in claim 1, which is selected from the group of consisting of:

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]benzyl)-2,4-thiazolidinedione; and 5-(4-[2-(N-methyl-N-(6-(4-(4-isopropyl)phenoxy)pyrimidinyl)amino)ethoxy]benzyl)-2,4-thiazolidinedione.

5. A diabetes therapeutic agent for oral administration, comprising an effective active component selected from a thiazolidinedione compound, represented in formula (1), a pharmaceutically acceptable salt thereof, or a pharmaceutically acceptable solvate thereof; and a pharmaceutically acceptable carrier:

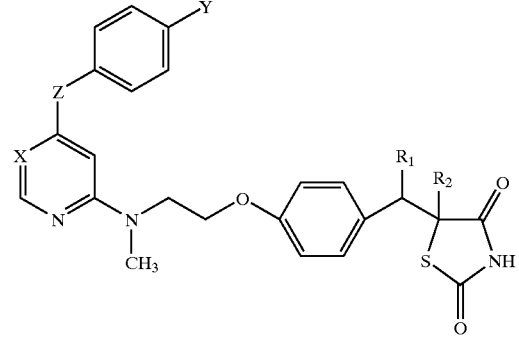

Formula (1)

wherein:
X represents a carbon or nitrogen atom; Y represents a hydrogen atom, a $C_1$–$C_4$ alkyl group, a $C_1$–$C_3$ alkoxy group, chlorine, fluorine or a phenyl group; Z represents NH, an oxygen, or sulfur atom; and $R_1$ and $R_2$ each represent a hydrogen atom, or $R_1$ and $R_2$ together form a bond.

6. The diabetes therapeutic agent for oral administration as set forth in claim 5, which has both a blood sugar lowering effect and a blood lipid lowering effect.

7. The diabetes therapeutic agent for oral administration as set forth in claim 5 or claim 6, wherein the effective active component is selected from the group consisting of:

5-(4-[2-(N-methyl-N-(6-(4-phenoxy)pyrimidinyl)amino)ethoxy]benzylidene)-2,4-thiazolidinedione;

5-(4-[2-(N-methyl-N-(6-(4-anilinyl)pyrimidinyl)amino)ethoxy]benzylidene)-2,4-thiazolidinedione;

5-(4-[2-(N-methyl-N-(2-(4-phenoxy)pyridinyl)amino)ethoxy]benzylidene)-2,4-thiazolidinedione;

5-(4-[2-(N-methyl-N-(6-(4-(4-fluoro)phenoxy)pyrimidinyl)amino)ethoxy]benzylidene)-2,4-thiazolidinedione;

5-(4-[2-(N-methyl-N-(6-(4-(4-chloro)phenoxy)pyrimidinyl)amino)ethoxy]benzylidene)-2,4-thiazolidinedione;

5-(4-[2-(N-methyl-N-(6-(4-(4-methoxy)phenoxy)pyrimidinyl)amino)ethoxy]benzylidene)-2,4-thiazolidinedione;

5-(4-[2-(N-methyl-N-(6-(4-(4-ethoxy)phenoxy)pyrimidinyl)amino)ethoxy]benzylidene)-2,4-thiazolidinedione;

5-(4-[2-(N-methyl-N-(6-(4-(4-isopropoxy) phenoxy)pyrimidinyl)amino)ethoxy]benzylidene)-2,4-thiazolidinedione;

5-(4-[2-(N-methyl-N-(6-(4-(4-methyl)phenoxy)pyrimidinyl)amino)ethoxy]benzylidene)-2,4-thiazolidinedione;

5-(4-[2-(N-methyl-N-(6-(4-(4-ethyl)phenoxy)pyrimidinyl)amino)ethoxy]benzylidene)-2,4-thiazolidinedione;

5-(4-[2-(N-methyl-N-(6-(4-(4-isopropyl)phenoxy)pyrimidinyl)amino)ethoxy]benzylidene)-2,4-thiazolidinedione;

5-(4-[2-(N-methyl-N-(6-(4-(4-phenyl)phenoxy)pyrimidinyl)amino)ethoxy]benzylidene)-2,4-thiazolidinedione;

5-(4-[2-(N-methyl-N-6-(4-thiophenoxy)pyrimidinyl)amino)ethoxy]benzylidene)-2,4-thiazolidinedione;

5-(4-[2-(N-methyl-N-(2-(4-(4-methoxy)phenoxy)pyridinyl)amino)ethoxy]benzylidene)-2,4-thiazolidinedione;

5-(4-[2-(N-methyl-N-(2-(4-(4-isopropyl)phenoxy)pyridinyl)amino)ethoxy]benzylidene)-2,4-thiazolidinedione;

5-(4-[2-(N-methyl-N-(2-(4-(4-fluoro)phenoxy)pyridinyl)amino)ethoxy]benzylidene)-2,4-thiazolidinedione;

5-(4-[2-(N-methyl-N-(2-(4-(4-chloro)phenoxy)pyridinyl)amino)ethoxy]benzylidene)-2,4-thiazolidinedione;

5-(4-[2-(N-methyl-N-(2-(4-thiophenoxy)pyridinyl)amino)ethoxy]benzylidene)-2,4-thiazolidinedione;

5-(4-[2-(N-methyl-N-(2-(4-anilinyl)pyridinyl)amino)ethoxy]benzylidene)-2,4-thiazolidinedione;

5-(4-[2-(N-methyl-N-(6-(4-phenoxy)pyrimidinyl)amino)ethoxy]benzyl)-2,4-thiazolidinedione;

5-(4-[2-(N-methyl-N-(6-(4-anilinyl)pyrimidinyl)amino)ethoxy]benzyl)-2,4-thiazolidinedione;

5-(4-[2-(N-methyl-N-(2-(4-phenoxy)pyridinyl)amino)ethoxy]benzyl)-2,4-thiazolidinedione;

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]benzyl)-2,4-thiazolidinedione;

5-(4-[2-(N-methyl-N-(6-(4-(4-ethoxy)phenoxy)pyrimidinyl)amino)ethoxy]benzyl)-2,4-thiazolidinedione;

5-(4-[2-(N-methyl-N-(6-(4-(4-isopropoxy)phenoxy)pyrimidinyl)amino)ethoxy]benzyl)-2,4-thiazolidinedione;

5-(4-[2-(N-methyl-N-(6-(4-(4-methyl)phenoxy)pyrimidinyl)amino)ethoxy]benzyl)-2,4-thiazolidinedione;

5-(4-[2-(N-methyl-N-(6-(4-(4-ethyl)phenoxy)pyrimidinyl)amino)ethoxy]benzyl)-2,4-thiazolidinedione;

5-(4-[2-(N-methyl-N-(6-(4-(4-isopropyl)phenoxy)pyrimidinyl)amino)ethoxy]benzyl)-2,4-thiazolidinedione;

5-(4-[2-(N-methyl-N-(6-(4-(4-phenyl)phenoxy)pyrimidinyl)amino)ethoxy]benzyl)-2,4-thiazolidinedione;

5-(4-[2-(N-methyl-N-(6-(4-thiophenoxy)pyrimidinyl)amino)ethoxy]benzyl)-2,4-thiazolidinedione;

5-(4-[2-(N-methyl-N-(2-(4-(4-fluoro)phenoxy)pyridinyl)amino)ethoxy]benzyl)-2,4-thiazolidinedione;

5-(4-[2-(N-methyl-N-(2-(4-(4-chloro)phenoxy)pyridinyl)amino)ethoxy]benzyl)-2,4-thiazolidinedione;

5-(4-[2-(N-methyl-N-(2-(4-(4-methoxy)phenoxy)pyridinyl)amino)ethoxy]benzyl)-2,4-thiazolidinedione;

5-(4-[2-(N-methyl-N-(2-(4-(4-isopropyl)phenoxy)pyridinyl)amino)ethoxy]benzyl)-2,4-thiazolidinedione;

5-(4-[2-(N-methyl-N-(2-(4-thiophenoxy)pyridinyl)amino)ethoxy]benzyl)-2,4-thiazolidinedione; and 5-(4-[2-(N-methyl-N-(2-(4-anilinyl)pyridinyl)amino)ethoxy]benzyl)-2,4-thiazolidinedione.

8. The diabetes therapeutic agent for oral administration as set forth in claim 5 or claim 6, wherein the effective active component is selected from the group consisting of:

5-(4-[2-(N-methyl-N-(6-(4-phenoxy)pyrimidinyl)amino)ethoxy]benzyl)-2,4-thiazolidinedione;

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]benzyl)-2,4-thiazolidinedione; and 5-(4-[2-(N-methyl-N-(6-(4-(4-isopropyl)phenoxy)pyrimidinyl)amino)ethoxy]benzyl)-2,4-thiazolidinedione.

9. The diabetes therapeutic agent for oral administration as set forth in claim 5 or claim 6, wherein the effective active component is selected from the group consisting of:

5-(4-[2-(N-methyl-N-(6-(4-phenoxy)pyrimidinyl)amino)ethoxy] benzylidene)-2,4-thiazolidinedione;

5-(4-[2-(N-methyl-N-(6-(4-anilinyl)pyrimidinyl)amino)ethoxy] benzylidene)-2,4-thiazolidinedione;

5-(4-[2-(N-methyl-N-(2-(4-phenoxy)pyrimidinyl)amino)ethoxy] benzylidene)-2,4-thiazolidinedione;

5-(4-[2-(N-methyl-N-(6-(4-(4-fluoro)phenoxy)pyrimidinyl)amino)ethoxy]-benzylidene)-2,4-thiazolidinedione;

5-(4-[2-(N-methyl-N-(6-(4-(4-chloro)phenoxy)pyrimidinyl)amino)ethoxy]-benzylidene)-2,4-thiazolidinedione;

5-(4-[2-(N-methyl-N-(6-(4-(4-methoxy)phenoxy)pyrimidinyl)amino)ethoxy]-benzylidene)-2,4-thiazolidinedione;

5-(4-[2-(N-methyl-N-(6-(4-(4-ethoxy)phenoxy)pyrimidinyl)amino)ethoxy]-benzylidene)-2,4-thiazolidinedione;

5-(4-[2-(N-methyl-N-(6-(4-(4-isopropoxy)phenoxy)pyrimidinyl)amino)ethoxy]-benzylidene)-2,4-thiazolidinedione;

5-(4-[2-(N-methyl-N-(6-(4-(4-methyl)phenoxy)pyrimidinyl)amino)ethoxy]-benzylidene)-2,4-thiazolidinedione;

5-(4-[2-(N-methyl-N-(6-(4-(4-ethyl)phenoxy)pyrimidinyl)amino)ethoxy]-benzylidene)-2,4-thiazolidinedione;

5-(4-[2-(N-methyl-N-(6-(4-(4-isopropyl)phenoxy)pyrimidinyl)amino)ethoxy]-benzylidene)-2,4-thiazolidinedione;

5-(4-[2-(N-methyl-N-(6-(4-(4-phenyl)phenoxy)pyrimidinyl)amino)ethoxy]-benzylidene)-2,4-thiazolidinedione;

5-(4-[2-(N-methyl-N-(6-(4-thiophenoxy)pyrimidinyl)amino)ethoxy]-benzylidene)-2,4-thiazolidinedione;

5-(4-[2-(N-methyl-N-(2-(4-(4-methoxy)phenoxy)pyridinyl)amino)ethoxy]-benzylidene)-2,4-thiazolidinedione;

5-(4-[2-(N-methyl-N-(2-(4-(4-isopropyl)phenoxy)pyridinyl)amino)ethoxy]-benzylidene)-2,4-thiazolidinedione;

5-(4-[2-(N-methyl-N-(2-(4-(4-fluoro)phenoxy)pyridinyl)amino)ethoxy]-benzylidene)-2,4-thiazolidinedione;

5-(4-[2-(N-methyl-N-(2-(4-(4-chloro)phenoxy)pyridinyl)amino)ethoxy]-benzylidene)-2,4-thiazolidinedione;

5-(4-[2-(N-methyl-N-(2-(4-thiophenoxy)pyridinyl)amino)ethoxy]benzylidene)-2,4-thiazolidinedione;

5-(4-[2-(N-methyl-N-(2-(4-anilinyl)pyridinyl)amino)ethoxy]benzylidene)-2,4-thiazolidinedione;

5-(4-[2-(N-methyl-N-(6-(4-phenoxy)pyrimidinyl)amino)ethoxy]benzyl)-2,4-thiazolidinedione;

5-(4-[2-(N-methyl-N-(6-(4-anilinyl)pyrimidinyl)amino)ethoxy]benzyl)-2,4-thiazolidinedione;

5-(4-[2-(N-methyl-N-(6-(4-phenoxy)pyridinyl)amino)ethoxy]benzyl)-2,4-thiazolidinedione;

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]-benzyl)-2,4-thiazolidinedione;

5-(4-[2-(N-methyl-N-(6-(4-(4-ethoxy)phenoxy)pyrimidinyl)amino)ethoxy]benzyl)-2,4-thiazolidinedione;

5-(4-[2-(N-methyl-N-(6-(4-(4-isopropoxy)phenoxy)pyrimidinyl)amino)ethoxy]-benzyl)-2,4-thiazolidinedione;

5-(4-[2-(N-methyl-N-(6-(4-(4-methyl)phenoxy)pyrimidinyl)amino)ethoxy]benzyl)-2,4-thiazolidinedione;

5-(4-[2-(N-methyl-N-(6-(4-(4-ethyl)phenoxy)pyrimidinyl)amino)ethoxy]benzyl)-2,4-thiazolidinedione;

5-(4-[2-(N-methyl-N-(6-(4-(4-isopropyl)phenoxy)pyrimidinyl)amino)ethoxy]-benzyl)-2,4-thiazolidinedione;

5-(4-[2-(N-methyl-N-(6-(4-(4-phenyl)phenoxy)pyrimidinyl)amino)ethoxy]benzyl)-2,4-thiazolidinedione;

5-(4-[2-(N-methyl-N-(6-(4-thiophenoxy)pyrimidinyl)amino)ethoxy]benzyl)-2,4-thiazolidinedione;

5-(4-[2-(N-methyl-N-(2-(4-(4-fluoro)phenoxy)pyridinyl)amino)ethoxy]benzyl)-2,4-thiazolidinedione;

5-(4-[2-(N-methyl-N-(2-(4-(4-chloro)phenoxy)pyridinyl)amino)ethoxy]benzyl)-2,4-thiazolidinedione;

5-(4-[2-(N-methyl-N-(2-(4-(4-methoxy)phenoxy)pyridinyl)amino)ethoxy]benzyl)-2,4-thiazolidinedione;

5-(4-[2-(N-methyl-N-(2-(4-(4-isopropyl)phenoxy)pyridinyl)amino)ethoxy]benzyl)-2,4-thiazolidinedione;

5-(4-[2-(N-methyl-N-(2-(4-thiophenoxy)pyridinyl)amino)ethoxy]benzyl)-2,4-thiazolidinedione; and 5-(4-[2-(N-methyl-N-(2-(4-anilinyl)pyridinyl)amino)ethoxy]benzyl)-2,4-thiazolidinedione.

10. The diabetes therapeutic agent for oral administration as set forth in claim 6, wherein the effective active component is selected from the group consisting of:

5-(4-[2-(N-methyl-N-(6-(4-phenoxy)pyrimidinyl)amino)ethoxy]benzyl)-2,4-thiazolidinedione;

5-(4-[2-(N-methyl-N-(6-(4-(4-fluoro)phenoxy)pyrimidinyl)amino)ethoxy]benzyl)-2,4-thiazolidinedione;

5-(4-[2-(N-methyl-N-(6-(4-(4-chloro)phenoxy)pyrimidinyl)amino)ethoxy]benzyl)-2,4-thiazolidinedione;

5-(4-[2-(N-methyl-N-(6-(4-(4-methoxy)phenoxy)pyrimidinyl)amino)ethoxy]-benzyl)-2,4-thiazolidinedione; and 5-(4-[2-(N-methyl-N-(6-(4-(4-isopropyl)phenoxy)pyrimidinyl)amino)ethoxy]-benzyl)-2,4-thiazolidinedione.

* * * * *